United States Patent
Otto et al.

(10) Patent No.: US 10,512,904 B2
(45) Date of Patent: Dec. 24, 2019

(54) ZEOLITIC MATERIALS HAVING ENCAPSULATED BIMETALLIC CLUSTERS

(71) Applicants: The Regents of the University of California, Oakland, CA (US); Chevron U.S.A. Inc., San Ramon, CA (US)

(72) Inventors: Trenton Otto, Berkeley, CA (US); Enrique Iglesia, Berkeley, CA (US); Stacey Ian Zones, San Francisco, CA (US)

(73) Assignees: The Regents of the University of California, Oakland, CA (US); Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/602,797

(22) Filed: May 23, 2017

(65) Prior Publication Data

US 2017/0341063 A1 Nov. 30, 2017

Related U.S. Application Data

(60) Provisional application No. 62/341,146, filed on May 25, 2016, provisional application No. 62/350,228, filed on Jun. 15, 2016.

(51) Int. Cl.
*B01D 53/86* (2006.01)
*B01J 23/42* (2006.01)
(Continued)

(52) U.S. Cl.
CPC .......... *B01J 29/74* (2013.01); *B01D 53/8628* (2013.01); *B01J 23/42* (2013.01); *B01J 23/44* (2013.01); *B01J 23/52* (2013.01); *B01J 35/0006* (2013.01); *B01J 35/0013* (2013.01); *B01J 37/009* (2013.01); *B01J 37/04* (2013.01); *B01J 37/10* (2013.01); *B01J 37/14* (2013.01);
(Continued)

(58) Field of Classification Search
None
See application file for complete search history.

(56) References Cited

U.S. PATENT DOCUMENTS

2016/0051971 A1 2/2016 Choi

OTHER PUBLICATIONS

Riahi et al, "Preparation, characterization and catalytic activity of gold-based nanoparticles on HY zeolites," Catalysis Today 72, pp. 115-121 (Year: 2002).*

(Continued)

*Primary Examiner* — Colin W. Slifka
(74) *Attorney, Agent, or Firm* — E. Joseph Gess; Terrance M. Flaherty; Melissa M. Hayworth

(57) ABSTRACT

Zeolites having highly dispersed bimetallic clusters, uniformly distributed in size and composition, encapsulated therein are disclosed. Metal encapsulation and alloying is conferred by introducing ligated metal cation precursors into zeolite synthesis gels, which are subsequently crystallized hydrothermally to form zeolites with metal cations occluded in the pores. The ligated cations are anchored to the zeolite framework via siloxane bridges which enforces their uniform dispersion throughout the zeolite crystals. Treatment of the crystallized zeolites in $O_2$ and then $H_2$ forms bimetallic clusters, which remain narrowly distributed in size and composition.

14 Claims, 12 Drawing Sheets

(51) Int. Cl.
| | |
|---|---|
| *B01J 23/44* | (2006.01) |
| *B01J 23/52* | (2006.01) |
| *B01J 29/74* | (2006.01) |
| *B01J 35/00* | (2006.01) |
| *B01J 37/00* | (2006.01) |
| *B01J 37/04* | (2006.01) |
| *B01J 37/10* | (2006.01) |
| *B01J 37/14* | (2006.01) |
| *B01J 37/18* | (2006.01) |
| *C07C 1/20* | (2006.01) |

(52) U.S. Cl.
CPC ................ *B01J 37/18* (2013.01); *C07C 1/20* (2013.01); *B01D 2255/50* (2013.01); *C07C 2523/42* (2013.01); *C07C 2523/44* (2013.01); *C07C 2523/52* (2013.01); *C07C 2529/74* (2013.01)

(56) References Cited

OTHER PUBLICATIONS

International Search Report and Written Opinion dated Aug. 2, 2017 in corresponding International Application No. PCT/2017/034024.

Riahi, G., et al., "Preparation, characterization and catalytic activity of gold-based nanoparticles on HY zeolites", Catalysis Today (2002) vol. 72, No. 1-2, pp. 115-121.

Otto, Trenton, et al., "Challenges and strategies in the encapsulation and stabilization of monodisperse Au clusters witin zeolites", Journal of Catalysis (2016) vol. 339, pp. 195-208.

Choi, Minkee, et al., "Mercaptosilane-Assisted Synthesis of Metal Clusters within Zeolites and Catalytic Consequences of Encapsulation", Journal of the American Chemical Society (2010) vol. 132, No. 26, pp. 9129-9137.

Otto, Trenton, et al., "Synthesis of stable monodisperse AuPd, AuPt, and PdPt bimetallic clusters encapsulated within LTA-zeolites", Journal of Catalysis, Academic Press, Duluth MN (2016) pp. 125-137.

\* cited by examiner

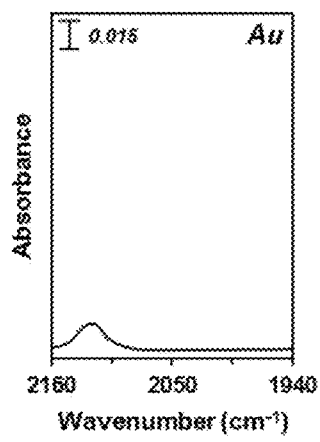
FIG. 5A
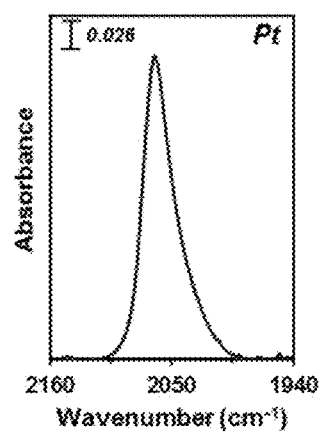
FIG. 5B
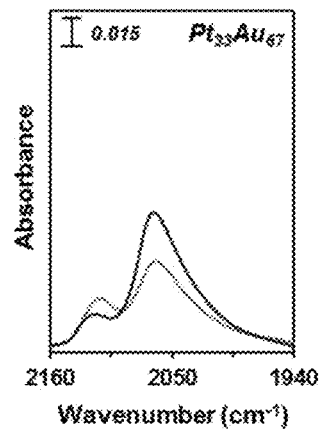
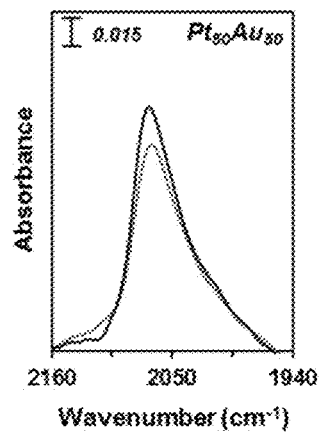
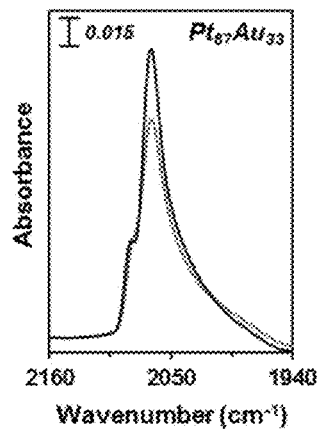
FIG. 5C FIG. 5D FIG. 5E

ZEOLITIC MATERIALS HAVING ENCAPSULATED BIMETALLIC CLUSTERS

CROSS REFERENCE TO RELATED APPLICATIONS

The present application claims priority to U.S. Provisional Application No. 62/341,146, filed May 25, 2016, and U.S. Provisional Application No. 62/350,228, filed Jun. 15, 2016, the disclosures of which are incorporated herein by reference in their entirety.

TECHNICAL FIELD

This disclosure relates to zeolites having alloyed bimetallic clusters encapsulated therein, methods for preparing the same, and uses thereof.

BACKGROUND

Bimetallic nanoparticle catalysts attract significant interest because of the unique electronic and structural characteristics of catalytically active mixed metal phases, which can confer synergistic enhancements over pure metals in the turnover frequency and selectivity of reactions as diverse as CO oxidation, alkane dehydrogenation, and $NO_x$ reduction. These enhancements in the rate and selectivity are often accompanied by further benefits for catalysis. The addition of a second metal may assist in the reduction of the first, improve the thermal stability of metals prone to cluster agglomeration, or preclude deactivation by sulfur or other poisons. Such effects may be brought forth by electronic modifications of the first metal with the second, which lead to partial charges that can alter adsorbate binding characteristics, or through coupled but distinct geometric effects in which small ensembles of the first metal are isolated and stabilized by the diluting metal. Rigorous studies that attempt to clearly distinguish these effects or provide a holistic mechanistic interpretation of the reactivity of bimetallic clusters require nanoparticles that are uniformly distributed in size and composition.

Strategies to prepare such well-defined alloys, however, often face synthetic challenges that preclude the achievement of these stringent requirements for cluster uniformity or may achieve this uniformity only at the expense of general applicability to clusters of diverse elemental composition.

Bimetallic clusters are most commonly prepared through the sequential adsorption and precipitation or co-impregnation of metal salts onto mesoporous scaffolds. Such techniques, however, suffer from an inability to carefully control the placement of the metals onto the support, and thus lead to bimodal mixtures of monometallic and bimetallic species. Controlled assembly techniques resolve these shortcomings through sequential grafting of organometallic compounds, first onto an oxide support and then onto the covalently anchored metal itself, where the latter step enforces strong metal-metal interactions that promote alloying. These techniques are limited to metals and metal complexes that selectively interact with each other instead of the support, and often form monometallic clusters of the second deposited metal. Galvanic displacement and electroless deposition methods, by contrast, allow the selective placement of a secondary metal onto pre-formed monometallic clusters through redox chemical reactions. These techniques typically result in bimetallic clusters uniformly distributed in composition, though their dispersion is ultimately limited to that of the monometallic seeding metal; the elements available for deposition onto these seeds are also restricted to metals with precursors stable against homogeneous nucleation of their monometallic clusters. Colloidal synthesis techniques, which typically proceed via the reduction of metal cation precursors in the presence of polymers that prevent agglomeration of the suspended nanoparticles, can produce bimetallic clusters that are uniformly distributed in composition and highly dispersed in size. The removal of the attached polymers, however, often requires treatment at elevated temperatures (>573 K), which can lead to sintering processes that compromise the intended size and compositional uniformity of the bimetallic clusters.

Alloy nanoparticles can alternatively be prepared within the voids of zeolite materials. Confinement within such voids leads to several and additional and distinct advantages for catalysis, including the protection of active metal surfaces from large poison species, the stabilization of specific transition states, and the reactant size selection properties that have made zeolites such ubiquitously useful catalysts. Metal encapsulation within zeolitic voids is achieved through the ion exchange of cationic metal precursors onto negatively charged sites in zeolite frameworks. Reductive treatment of these exchanged zeolites forms monometallic clusters dispersed throughout the zeolitic voids, after which the exchange and reduction of a second metal forms encapsulated bimetallic clusters. Such techniques have been successfully implemented to prepare encapsulated alloy clusters stable against sintering at temperatures in excess of 573 K, although the successive ion exchange process does not guarantee uniform compositions and is limited to zeolites with pore apertures wide enough for solvated metal cations to enter the framework. The apertures within small-pore and medium-pore zeolites preclude post-synthetic encapsulation protocols via ion-exchange from aqueous media, which require the migration of solvated metal-oxo oligomers that cannot diffuse through the small apertures in such zeolites.

According to the present disclosure, bimetallic clusters narrowly distributed in size and composition have now been encapsulated within the voids of zeolites that preclude post-synthetic encapsulation protocols via a ligand-assisted hydrothermal synthesis technique.

SUMMARY

In one aspect, the invention resides in an aluminosilicate zeolite having an alloyed bimetallic cluster encapsulated in the pores of the aluminosilicate zeolite.

In another aspect, the invention resides in a method of synthesizing the aluminosilicate zeolite described herein, the method comprising the steps of: (a) preparing a reaction mixture capable of forming the zeolite, the reaction mixture comprising: a source of silicon oxide; a source of aluminum oxide; a source of a Group 1 or 2 metal (X); hydroxide ions; sources of a first metal precursor ($M_1$) and a second metal precursor ($M_2$) of Groups 8 to 12 of the Periodic Table of the Elements; a ligating agent (L) having a thiol group and an alkoxysilyl group; and water; (b) heating the reaction mixture under crystallization conditions including a temperature of 85° C. to 180° C. and a time from 5 to 250 hours until crystals of the aluminosilicate zeolite are formed; (c) recovering the aluminosilicate zeolite from step (b); (d) contacting the aluminosilicate zeolite of step (c) with oxygen under oxidative conditions including a temperature of 250° C. to 500° C. and a time of 0.5 to 5 h; and (e) contacting the oxidized aluminosilicate zeolite of step (d) with hydrogen under reductive conditions including a temperature of 250° C. to 500° C. and a time of 0.5 to 5 h.

In a further aspect, the invention resides in a process for converting a feedstock comprising an organic compound to a conversion product that comprises the step of contacting the feedstock with a catalyst at organic compound conversion conditions, the catalyst comprising the aluminosilicate zeolite material described herein.

In yet a further aspect, the invention resides in a process for selectively reducing nitrogen oxides ($NO_x$), the process comprising contacting a gaseous stream containing $NO_x$ with a catalyst comprising the aluminosilicate zeolite material described herein.

BRIEF DESCRIPTION OF THE DRAWINGS

FIG. 2A shows the TEM for AuNaLTA; FIG. 2B shows the TEM for $Au_{50}Pd_{50}$NaLTA; FIG. 2C shows the TEM for PdNaLTA; FIG. 2D shows the TEM for $Au_{50}Pt_{50}$NaLTA; FIG. 2E shows the TEM for PtNaLTA; and FIG. 2F shows the TEM for $Pd_{65}PT_{35}$NaLTA.

FIGS. 5A-5E show the infrared (IR) spectra of carbon monoxide (CO) adsorbed on monometallic or bimetallic $Au_nPd_{100-n}$CaLTA samples (1 kPa CO, 99 kPa He) at 278 K after $H_2$ treatment (573 K, 20 kPa $H_2$, 80 kPa He) (gray spectra) and after heating in CO (1 kPa CO, 99 kPa He) up to 353 K (black spectra). FIG. 5A shows the spectrum for Au; FIG. 5B shows the spectrum for Pt; FIG. 5C shows the spectrum for $Pt_{33}Au_{67}$; FIG. 5D shows the spectrum for $Pt_{50}Au_{50}$; and FIG. 5E shows the spectrum for $Pt_{67}Au_{33}$.

FIG. 6A shows the spectrum for Au; FIG. 6B shows the spectrum for Pd; FIG. 6C shows the spectrum for $Pd_{33}Au_{67}$; FIG. 6D shows the spectrum for $Pd_{50}Au_{50}$; and FIG. 6E shows the spectrum for $Pd_{67}Au_{33}$.

DETAILED DESCRIPTION

Introduction

Figure 1:
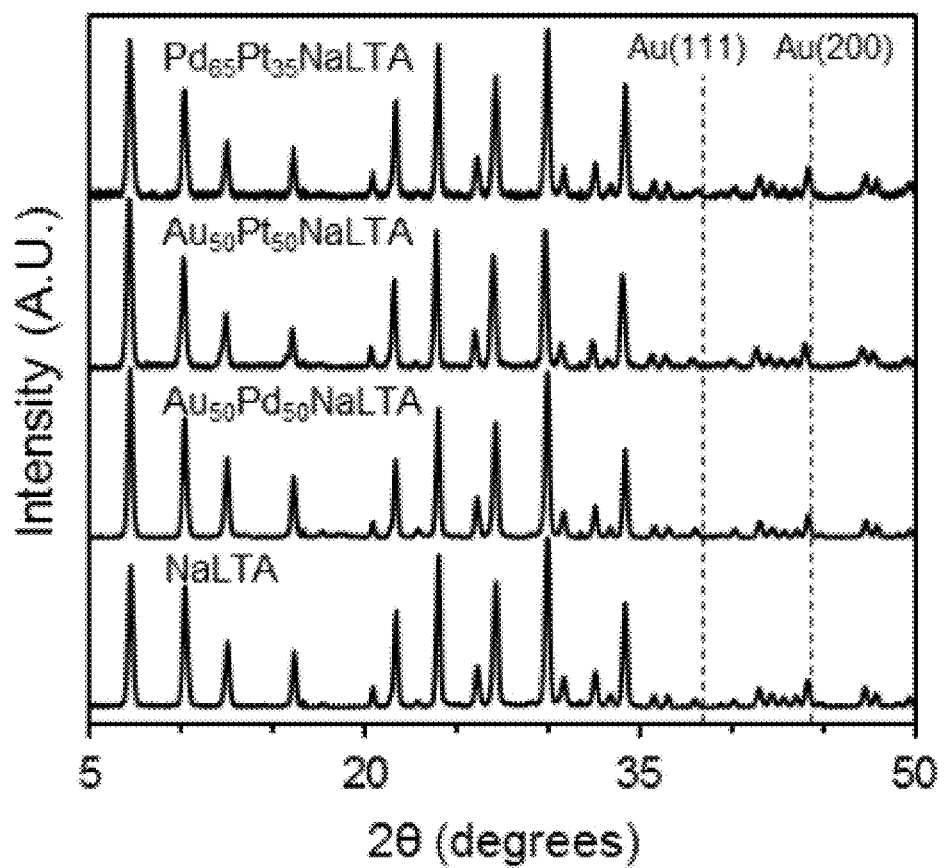
FIG. 1 shows the powder X-ray diffraction (XRD) patterns of several bimetallic metal-zeolite samples and a metal-free NaLTA zeolite standard.
Figure 2A:
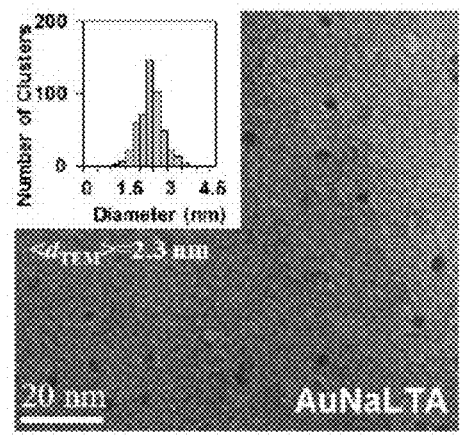
FIGS. 2A-2F show transmission electron micrographs (TEM) and particle size distributions for a selection of monometallic and bimetallic metal zeolite samples.
Figure 2B:
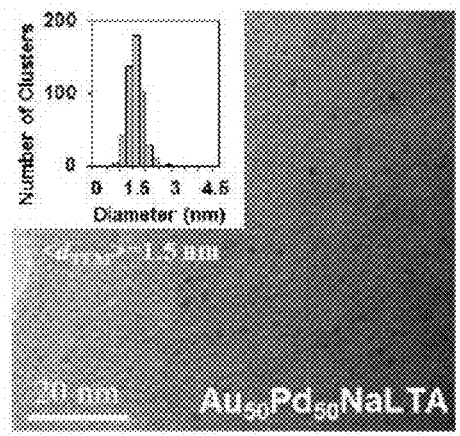
Figure 2C:
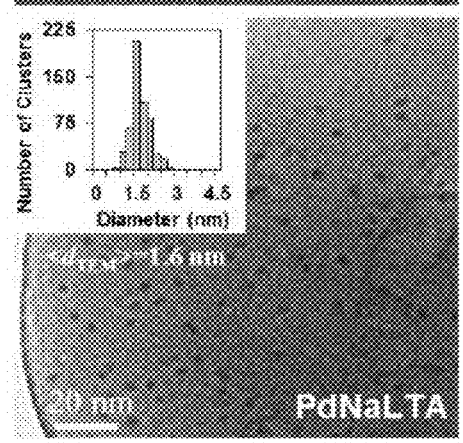
Figure 2D:
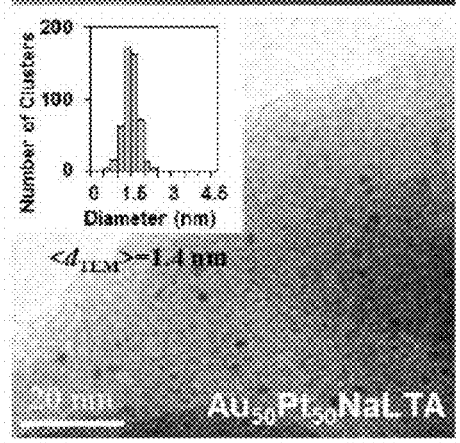
Figure 2E:
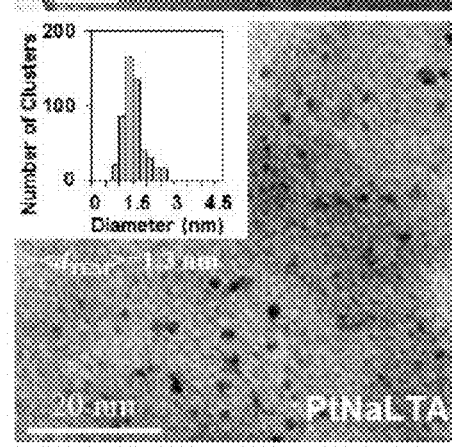
Figure 2F:
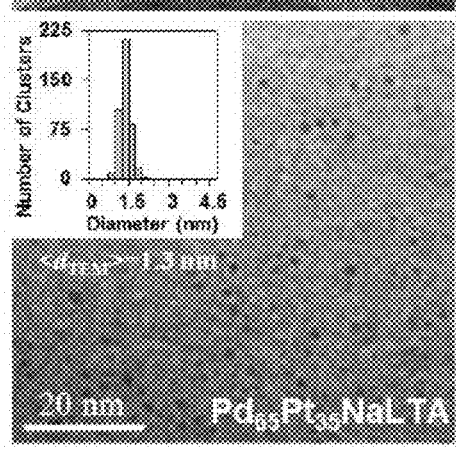

The term "alloy" refers to a bonding structure of two or more elements in their reduced or partially reduced forms without limitation to any specific coordination or elemental identity among the elements present.

The term "cluster" refers to identifiable associations of 2 or more atoms. Such associations are typically established by some type of bond—ionic, covalent, Van der Waals, and the like.

The term "encapsulated" refers to substances that are completely surrounded by another material. In the context of the present disclosure, an encapsulated metal is a metal enclosed within microporous zeolite voids.

The powder X-ray diffraction (XRD) data reported herein were collected with a D8 Discover GADDS Powder Diffractometer with Cu-K□ radiation (□=0.15418 nm, 40 kV, 40 mA). The samples were first ground to fine powders, then placed and leveled on quartz slides for the measurements. Diffractograms were measured for 2θ values ranging from 5-50° and a scan rate of 0.00625 degrees $s^{-1}$.

The transmission electron micrographs (TEM) reported herein were collected with a Philips/FEI Technai 12 microscope. Samples for TEM imaging were prepared by dispersing finely ground powders in acetone and depositing them onto holey carbon films supported on 400 mesh copper grids (Ted Pella Inc.). Metal cluster size distributions were measured from >300 particles for each sample, and used to determine surface-averaged cluster diameters $\langle d_{TEM} \rangle$ according to Equation (1):

$$\langle d_{TEM} \rangle = \frac{\sum n_i d_i^3}{\left| \sum n_i d_i^2 \right.} \quad (1)$$

where $n_i$ is the number of clusters with diameter $d_i$. These size distributions were further used to calculate dispersity index (DI) values, which are given by the ratio of the surface-averaged ($\langle d_{TEM} \rangle$) to the number-averaged ($\langle d_n \rangle$) diameter according to Equation 2:

$$DI = \frac{\langle d_{TEM} \rangle}{\langle d_n \rangle} = \frac{\left(\frac{\sum n_i d_i^3}{\sum n_i d_i^2}\right)}{\left(\frac{\sum n_i d_i}{\sum n_i}\right)} \quad (2)$$

The DI value indicates the particle size uniformity, with unity corresponding to perfect monodispersity and values <1.5 taken as nearly monodisperse distributions. DI values are not widely reported despite IUPAC guidelines; therefore, standard deviations of the mean particle diameters are also reported here to provide a second metric of the particle size uniformity.

Metal dispersions (D), defined as the fraction of metal atoms exposed at cluster surfaces, were estimated from $\langle d_{TEM} \rangle$ according to Equation (3):

$$D = 6 \frac{\bar{v}_m / \bar{a}_m}{\langle d_{TEM} \rangle} \quad (3)$$

where $\bar{v}_m$ is the effective bulk atomic density of the bimetallic samples, estimated as the composition-weighted average of the $v_m$ values for pure Au ($16.49 \times 10^{-3}$ nm$^3$), Pd ($14.70 \times 10^{-3}$ nm$^3$), or Pt ($15.10 \times 10^{-3}$ nm$^3$). The value of $\bar{a}_m$, the effective area occupied by a metal atom on polycrystalline surfaces, was also calculated as a composition-weighted mean from the pure component values (Au: $8.75 \times 10^{-2}$ nm$^2$; Pd: $7.93 \times 10^{-2}$ nm$^2$; Pt: $8.07 \times 10^{-2}$ nm$^2$).

UV-visible spectra of synthesized and treated metal-zeolite samples reported herein were acquired using a Varian-Cary 6000i spectrometer with a Harrick scientific diffuse reflectance accessory (DRP-XXX) and a reaction chamber add-on (DRA-2CR). The spectra were collected under 100 kPa of He at ambient temperature for AuNaLTA, Au$_n$Pd$_{100-n}$NaLTA, and Au$_n$Pt$_{100-n}$NaLTA (0.1 g each) powders, which were ground and sieved to retain <100 μm aggregates. Background spectra were used to isolate the effect of the embedded metals on the spectral absorbance, and were collected on NaLTA samples synthesized and treated as the metal-NaLTA.

Infrared (IR) spectra of CO adsorbed on Au$_n$Pd$_{100-n}$CaLTA, Au$_n$Pt$_{100-n}$CaLTA, and Pd$_n$Pt$_{100-n}$CaLTA wafers (40 mg cm$^{-2}$) were collected to probe the surface compositions of metal particles. Spectra reported herein were acquired with a Thermo Nicolet 8700 spectrometer equipped with an in situ flow cell. All sample wafers were first heated in flowing H$_2$/He mixtures (8.4 cm$^3$ g$^{-1}$ s$^{-1}$ H$_2$, 33.6 cm$^3$ g$^{-1}$ s$^{-1}$ He) from ambient temperature to 573 K (0.033 K s$^{-1}$) for 1 h. The Pd$_n$Pt$_{100-n}$CaLTA samples were then rapidly cooled in He flow (42.0 cm$^3$ g$^{-1}$ s$^{-1}$) to 313 K (−0.17 K s$^{-1}$), and exposed to flowing CO/He (42.0 cm$^3$ g$^{-1}$ s$^{-1}$; 1.0 kPa CO) before collecting IR spectra. Au$_n$Pd$_{100-n}$CaLTA samples, after the H$_2$/He treatment at 573 K, were instead cooled to 278 K (−0.17 K s$^{-1}$), in flowing He (42.0 cm$^3$ g$^{-1}$ s$^{-1}$), after which spectra were also collected under flowing CO/He (42.0 cm$^3$ g$^{-1}$ s$^{-1}$; 1.0 kPa CO). The Au$_n$Pd$_{100-n}$CaLTA samples were then heated in this flowing CO/He to 353 K (0.033 K s$^{-1}$) for 0.5 h, and then cooled back to 278 K (−0.17 K s$^{-1}$) under continuous CO flow at which time a second spectrum was collected. Au$_n$Pt$_{100-n}$CaLTA samples were treated analogously to Au$_n$Pd$_{100-n}$CaLTA, except they were cooled to 263 K instead of 278 K. The AuPd and AuPt bimetallic samples were subjected to this intermittent period of CO exposure and heating with the intent of inducing changes in the surface compositions of alloyed clusters. The NaLTA zeolites (0.42 nm apertures), produced by the synthesis procedures reported herein, were exchanged with Ca$^{2+}$ (forming CaLTA; 0.50 nm apertures) before these experiments to enlarge pore windows and improve the accessibility of CO to the zeolite interior. Spectral contributions from CO(g) and Ca$^{2+}$—CO complexes were subtracted from all reported spectra.

X-Ray absorption spectroscopy (XAS) data reported herein was performed at the Au-L$_3$ edge (11,919 eV), Pd—K edge (24,350 eV), and Pt-L$_3$ edge (11,564 eV) using the XDS beamline of the LNLS (Laboratório Nacional do Luz Síncrotron, Campinas, Brazil). Two-crystal Si(311) or Si(111) monochromators were employed for absorption measurements at the Pd—K edge or Au-L$_3$ and Pt-L$_3$ edges, respectively; harmonic beam components were less than 1% using these monochromators. All experiments were performed in transmission mode, and beam intensities were measured using a series of three ionization chambers filled with a mixture of N$_2$ and Ar at ambient temperature and a pressure of 1 bar. The photon energies were calibrated by measuring the beam transmission, simultaneously with the sample, through a thin film of metallic foil (Au, Pd, or Pt) placed between the second and third ionization chambers. XAS spectra were measured for Au$_{50}$Pd$_{50}$NaLTA and Pd$_{65}$Pt$_{35}$NaLTA samples; spectra of bimetallic samples were collected at the absorption edges of both metals present (Au-L$_3$ and Pd—K, or Pd—K and Pt-L$_3$) in a range of 200 eV before and 1000 eV after the corresponding edge. The samples (0.1 g each) were prepared first with treatment in flowing 10% H$_2$/Ar (1.67 cm$^3$ g$^{-1}$ s$^{-1}$) at 573 K (0.033 K s$^{-1}$) for 1 h, then cooled to ambient temperature under Ar flow (1.67 cm$^3$ g$^{-1}$ s$^{-1}$). They were then transferred under Ar at atmospheric pressure and ambient temperature to an XAS cell hermetically sealed with KAPTON® windows. The samples were stored in this cell for ~10 h, after which the XAS spectra were collected at ambient temperature.

Extended X-ray absorption fine structure (EXAFS) data analyses reported herein was carried out using the IFFEFIT package (Athena, Artemis). Background subtraction and edge-step normalization of the spectra were performed using the AUTOBK algorithm implemented in Athena. Structural information for the metals, including coordination numbers (N), interatomic distances (D), and their Debye-Waller factors ($\sigma^2$), were obtained from Artemis using nonlinear least squares fits of the Fourier transformed data in r-space, with theoretical amplitudes and phase shifts for all single scattering paths calculated by FEFF (see S. I. Zabinsky et al., *Phys. Rev. B* 1995, 52, 2995-3009). All data fits were conducted between 1.0-3.0 Å in r-space and were generated by Fourier filtering the k$^3$-weighted EXAFS over 2-13 Å$^{-1}$ in k-space with a Hanning window. The theoretical scattering path amplitudes and phase shifts used in these fits were calculated from crystallographic structures of either monometallic lattices (for Au—Au, Pd—Pd, and Pt—Pt paths) or mixed phase lattices (for Pd—Au and Pd—Pt paths), all of which are face-centered cubic (FCC). The first coordination shell of the absorbing atom in these bimetallic lattices was filled with like or dislike atoms in proportions that reflect the molar ratio of metals measured in each sample by ICP. EXAFS data extracted from bimetallic samples were fit simultaneously at both metal edges, thus ensuring consistency in the interatomic distances and Debye-Waller factors of bimetallic paths. Photoelectron single scattering by low-Z species (O and S), with theoretical amplitudes and phases calculated from metal oxide (PdO, PtO) or metal sulfide (PdS, PtS, Au$_2$S$_3$) crystal structures, were also included in the fits to examine the contribution of these nonmetallic bonds to the EXAFS. Passive reduction factors (S$_0^2$) for each metal (Au: 0.95, Pd: 0.83, Pt: 0.96) were obtained from single scattering fits to the EXAFS spectra of the metal foils by constraining the coordination number to 12 in each case.

Metal contents in the synthesized and treated samples reported herein were measured by inductively coupled plasma optical emission spectroscopy (ICP-OES) using a Perkin Elmer 5300 DV optical emission ICP analyzer.

Reaction Mixture

In general, the zeolite is synthesized by: (a) preparing a reaction mixture containing (1) a source of silicon oxide; (2) a source of aluminum oxide; (3) a source of a Group 1 or 2 metal (X); (4) hydroxide ions; (5) sources of a first metal precursor (M$_1$) and a second metal precursor (M$_2$) of Groups 8 to 12 of the Periodic Table of the Elements; (6) a ligating agent (L) having a thiol group and an alkoxysilyl group; and (7) water; and (b) subjecting the reaction mixture to crystallization conditions sufficient to form crystals of the zeolite.

The relative amounts of reagents added to the reactor to form the reaction mixture will also vary in a known manner according to the target zeolite. Thus, in one embodiment, where the target zeolite has the LTA framework type, the composition of the reaction mixture from which the zeolite is formed, in terms of mole ratios, is identified in Table 1 below:

TABLE 1

| Reactants | Useful | Exemplary |
| --- | --- | --- |
| SiO$_2$/Al$_2$O$_3$ | ≥1 | 1 to 500 |
| X/SiO$_2$ | 0.25 to 1.00 | 0.25 to 1.00 |
| OH/SiO$_2$ | 0.25 to 1.00 | 0.25 to 1.00 |
| (M$_1$ + M$_2$)/SiO$_2$ | 0.005 to 0.025 | 0.005 to 0.020 |
| L/SiO$_2$ | 0.02 to 0.25 | 0.02 to 0.20 |
| H$_2$O/SiO$_2$ | ≥50 | 50 to 100 | wherein compositional variables X, M$_1$, M$_2$, and L are as described herein above.

Suitable sources of silicon oxide include fumed silica, colloidal silica, precipitated silica, alkali metal silicates, and tetraalkyl orthosilicates.

Suitable sources of aluminum oxide include hydrated alumina and water-soluble aluminum salts (e.g., aluminum nitrate).

Sources of Group 1 or 2 metal include metal oxide, metal chloride, metal fluoride, metal sulfate, metal nitrate, or metal aluminate.

Combined sources of two or more of the components X, Al$_2$O$_3$ and SiO$_2$ can also be used and can include, for example, sodium aluminate, clays or treated clays (e.g., metakaolin), and aluminosilicate zeolites (e.g., BEA and FAU framework type aluminosilicate zeolites).

The metal of the first and second metal precursors may be selected from Fe, Ru, Os, Co, Rh, Pd, Pt, Cu, Ag, and Au. Suitably, the metal of the first and second metal precursors may be selected from Pd, Pt, and Au. The second metal precursor is different from the first metal precursor. The metal precursor can be an amine or ethylene diamine complex. The metal precursor can also be a ligated metal.

The ligating agent is an organic compound having a thiol group and an alkoxysilyl group. Suitable ligating agents include 3-mercaptopropyltrimethoxysilane, 3-mercaptopropyltriethoxysilane, 3-mercaptopropylmethyldimethoxysilane, (mercaptomethyl)dimethylethoxysilane, and mercaptomethyltrimethoxysilane.

Without being bound by any particular theory, it is believed that the thiol group (—SH) in the ligating agent binds strongly to late transition metals to form stable metal-sulfur adducts via ligand-exchange. These metal-sulfur adducts are resistant to formation of bulk metal hydroxides even at the high pH required for zeolite synthesis. Moreover, the alkoxysilyl group of the ligating agent undergoes hydrolysis in alkaline media to form covalent Si—O—Si or Si—O—Al bonds with nucleating zeolite structures, thereby forming linkages that enforce metal encapsulation during subsequent zeolite crystal growth.

The mole ratio of ligating agent to the first and second metal precursors [L/(M$_1$+M$_2$)] in the reaction mixture may range from 4 to 10 (e.g., from 5 to 8).

The reaction mixture may also contain seeds of a zeolite material desirably in an amount of from 0.01 to 10,000 ppm by weight (e.g., from 100 to 5000 ppm by weight) of the reaction mixture.

The reaction mixture is substantially free of organotemplate materials, wherein "substantially" as employed herein with respect to the amount of one or more organotemplates contained in the one or more materials used in a synthetic process indicates an amount of 0.001 wt. % or less (e.g., 0.0005 wt. % or less, or 0.00001 wt. %) of one or more organotemplates. The amounts of one or more organotemplates, if at all present in any one of the materials used in the synthetic process, may also be denoted as "impurities" or "trace amounts" within the meaning of the present disclosure. The term "organotemplate" as employed in the present disclosure designates any conceivable organic material which is suitable for template-mediated synthesis of a zeolite material, such as a zeolite having a framework type selected from the group consisting of CHA, ERI, EUO, FER, GIS, HEU, KFI, LEV, LTA, MEL, MFI, MFS, MTT, MTW, RTH, SOD, TON, and combinations thereof (e.g., a zeolite having the LTA framework type).

The reaction mixture can be prepared either batch wise or continuously. Crystal size, morphology and crystallization time of the zeolite described herein can vary with the nature of the reaction mixture and the crystallization conditions.

Crystallization and Post-Synthesis Treatment

Crystallization of the zeolite disclosed herein can be carried out under either static, tumbled or stirred conditions in a suitable reactor vessel, such as polypropylene jars or Teflon-lined or stainless steel autoclaves, at a temperature of from about 85° C. to 180° C. for a time sufficient for crystallization to occur at the temperature used, e.g., from 5 to 250 hours. The reaction mixture may be reacted under autogenous pressure, or optionally in the presence of a gas such as nitrogen.

Once the zeolite crystals have formed, the solid product is separated from the reaction mixture by standard mechanical separation techniques such as centrifugation or filtration. The crystals are water-washed and then dried to obtain the as-synthesized zeolite crystals. The drying step is typically performed at a temperature below 200° C.

The as-synthesized zeolite is then subjected to sequential oxidative and reductive treatments in the presence of oxygen and hydrogen, respectively. Sequential oxidative and reductive treatment of the zeolite results in the formation of bimetallic clusters, which remain narrowly distributed in size. The reduced material is typically passivated prior to exposure to ambient air.

Conditions for oxidative and reductive treatment include heating the zeolite to a temperature from 250° C. to 500° C. for an appropriate period of time (e.g. 0.5 to 5 h, or 1 to 3 h) under ambient pressure. Treatment of the as-synthesized zeolite under oxidative conditions also facilitates removal of any of the organic moieties used in its synthesis.

Characterization of the Zeolite

The zeolite formed by the process described herein may be a small-pore zeolite or a medium-pore zeolite. A small-pore size zeolite has an average pore size from 3 Å (0.3 nm) to less than 5.0 Å (0.5 nm) and includes, for example, CHA, ERI, GIS, KFI, LEV, LTA, RTH, and SOD framework type zeolites (IUPAC Commission of Zeolite Nomenclature). A medium-pore size zeolite has an average pore diameter 5 Å (0.5 nm) to 7 Å (0.7 nm) and includes for example, EUO, FER, HEU, MEL, MFI, MFS, MTT, MTW, and TON framework type zeolites (IUPAC Commission of Zeolite Nomenclature). In one embodiment, the zeolite formed by the processed described herein has the LTA framework type.

The apertures of small- and medium-pore zeolites preclude conventional post-synthetic encapsulation protocols via ion exchange from aqueous media, which require migration of solvated metal-oxo oligomers that cannot diffuse through the small apertures in such zeolites (e.g., divalent and higher in small-pore zeolites and trivalent and higher in medium-pore zeolites).

The encapsulated bimetallic clusters of the zeolite disclosed herein may be characterized as having a small size. The encapsulated clusters may have a surface weighted mean cluster diameter $\langle d_{TEM} \rangle$ of 1.0 to 2.0 nm (e.g., 1.1 to 1.9 nm, 1.2 to 1.8 nm, or 1.3 to 1.7 nm). The surface area weighted mean cluster diameter is determined via TEM (see Equation 1).

The encapsulated bimetallic clusters of the zeolite disclosed herein may be characterized as having a narrow size distribution. The encapsulated clusters may have a dispersity index of 1.50 or less (e.g., 1.00 to 1.50, 1.00 to 1.25, 1.00 to 1.15, 1.05 to 1.50, 1.05 to 1.25, or 1.05 to 1.15). The dispersity index is computed as the surface averaged cluster diameter divided by the number averaged diameter (see Equation 2).

The collective amount of metals of Groups 8 to 12 can be from 0.1 to 5.0 wt. % (e.g., 0.1 to 2.5 wt. %, 0.1 to 2.0 wt. %, 0.1 to 1.5 wt. %, 0.3 to about 5.0 wt. %, or 0.3 to 2.5 wt. %, 0.3 to 1.5 wt. %, 0.5 to 5.0 wt. %, 0.5 to 2.5 wt. %, or 0.5 to 1.5 wt. %), based on the total weight of the composite.

The metals in the encapsulated bimetallic clusters of the zeolite disclosed herein may have a metal ratio of the first metal to the second metal of from 99:1 to 1:99 (e.g., 95:5 to 5:95, 75:25 to 25:75, or 60:40 to 40:60). The bimetallic metals may be selected from Groups 8 to 12 of the Periodic Table of Elements. The bimetallic metals may consist of gold and palladium, gold and platinum, or palladium and platinum.

Processes Using the Zeolite

The zeolite of the present disclosure can be used as a catalyst to catalyze a wide variety of organic compound conversion processes including many of present commercial/industrial importance. Examples of organic conversion processes which may be catalyzed by the present zeolite include alkylation, (hydro)cracking, disproportionation, (hydro)isomerization, oligomerization, and conversion of oxygenates to one or more olefins, particularly ethylene and propylene.

The zeolite of the present disclosure can be used as a catalyst for the catalytic reduction of nitrogen oxides in a gas stream.

As in the case of many catalysts, it may be desirable to incorporate the present zeolite with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring, or in the form of gelatinous precipitates or gels, including mixtures of silica and metal oxides. Use of a material in conjunction with the present zeolite, i.e., combined therewith or present during synthesis of the material, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays (e.g., bentonite and kaolin) to improve the crush strength of the catalyst under commercial operating conditions. These materials (i.e., clays, oxides, etc.) function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays that can be composited with the present zeolite include those in the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present molecular sieve also include inorganic oxides, such as silica, zirconia, titania, magnesia, beryllia, alumina, and mixtures thereof.

In addition to the above mentioned materials, the present zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of the present zeolite and inorganic oxide matrix may vary widely, with the content of the present zeolite ranging from 1 to 90 wt. % (e.g., 2 to 80 wt. %) of the composite.

EXAMPLES

The following illustrative examples are intended to be non-limiting.

Preparation of Zeolite-Encapsulated Au, Pd, Pt and Bimetallic AuPd, AuPt, and PdPt Clusters Preparation procedures for bimetallic metal-encapsulated Na-LTA zeolites ($M_1M_2$NaLTA, where $M_1$ and $M_2$ are Au, Pd, or Pt) were adapted from hydrothermal synthesis protocols for their monometallic counterparts (see, M. Choi et al., *J. Am. Chem. Soc.* 2010, 132, 9129-9137; and T. Otto et al., *J. Catal.* 2016, 339, 195-208) and modified to incorporate multiple metal cation species into zeolite synthesis gels.

Synthetic protocols for the three monometallic samples (AuNaLTA, PdNaLTA, and PtNaLTA) and bimetallic samples (Au$_n$Pd$_{100-n}$NaLTA, Au$_n$Pt$_{100-n}$NaLTA, and Pd$_n$Pt$_{100-n}$NaLTA, where 0≤n≤100 and indicates the relative % molar quantity of included metal) follow analogous procedures, which differ only in the identity and fractional amounts of noble metal cations added to each gel.

In the synthesis of Au$_{50}$Pd$_{50}$NaLTA, for example, the protecting ligand 3-mercaptopropyl-trimethoxysilane (0.96 g) and NaOH (4.8 g) were first dissolved in deionized H$_2$O (17.9 MΩ resistance; 18 mL) within an open 125 mL polypropylene bottle and magnetically stirred (6.7 Hz; 8 h). Aqueous solutions of HAuCl$_4$·3H$_2$O (0.156 g in 9 mL deionized H$_2$O) and Pd(NO$_3$)$_2$ (0.118 g in 9 mL deionized H$_2$O) were then added simultaneously and dropwise to the basic ligand solution over a period of 0.5 h as the mixture was continuously agitated with a magnetic bar (6.7 Hz). Colloidal silica (10.67 g, LUDOX® AS-30) was then added to the polypropylene bottle, which was sealed with its cap and heated to 353 K for 0.5 h, also with continuous magnetic bar agitation (6.7 Hz). An aqueous solution of NaAlO$_2$ (6.0 g in 18 mL deionized H$_2$O) was then added dropwise to the silica, ligand, and metal cation solution and allowed to mix by magnetic stirring (6.7 Hz) for 2 h at ambient temperature; this mixing led to a homogeneous synthesis gel with molar ratios of 1.7 SiO$_2$/1 Al$_2$O$_3$/3.2 Na$_2$O/110 H$_2$O/0.013 Au/0.013 Pd/0.156 ligand. Finally, the gel was heated to 373 K with continuous magnetic stirring (6.7 Hz) for 12 h to form Au$_{50}$Pd$_{50}$NaLTA. The solids formed by this process were filtered (Pyrex 3606 fritted funnel, 4-5.5 μm), washed with deionized H$_2$O until the rinse liquids reached a pH 7-8, and treated in a convection oven at 373 K for 8 h. The solids were then heated in flowing dry air (1.67 cm$^3$ g$^{-1}$ s$^{-1}$) from ambient temperature to 623 K (0.033 K s$^{-1}$) and held for 2 h, cooled to ambient temperature, and then heated to 623 K (0.033 K s$^{-1}$) in flowing H$_2$ (1.67 cm$^3$ g$^{-1}$ s$^{-1}$) and held for 2 h. A final heating procedure in air (1.67 cm$^3$ g$^{-1}$ s$^{-1}$) at 723 K (0.033 K s$^{-1}$) was then conducted for 2 h.

The molar ratio of the two metals present in each bimetallic sample was adjusted by varying the relative amounts of noble metal cation precursors (HAuCl$_4$·3H$_2$O, Pd(NO$_3$)$_2$, or H$_2$PtCl$_6$) added to the gel, while keeping the total metal content fixed at 1.0 wt. % theoretical loading. Monometallic metal-zeolite samples were also synthesized with 1.0 wt. % theoretical loading. The molar ratio of 3-mercaptopropyl-trimethoxysilane to the added metals was kept fixed at 6 for each sample synthesis, regardless of the identity of the metal cations used.

The air and H$_2$ treated metal-NaLTA samples were exchanged with Ca$^{2+}$ ions to convert the host zeolite CaLTA before use in infrared studies. The calcium exchange was performed by adding monometallic or bimetallic metal-zeolite samples (1-5 g) to an aqueous 1 M solution of CaCl$_2$·2H$_2$O (1 g zeolite per 100 mL) and stirring magnetically (6.7 Hz) at ambient temperature for 8 h. The exchange was repeated ten times to ensure full Ca$^{2+}$ exchange, and the solids were filtered and washed with deionized water (1500 mL g$^{-1}$), and finally treated in ambient air within a convection oven at 373 K for 12 h.

Synthesis of Au, Pd, and Pt Clusters on Mesoporous SiO$_2$

Au, Pd, and Pt clusters dispersed on mesoporous SiO$_2$ were synthesized and used as oxidative dehydrogenation (ODH) catalysts for comparison with the bimetallic clusters supported by zeolites. Pd/SiO$_2$ and Pt/SiO$_2$ catalysts were prepared with incipient wetness impregnation using aqueous solutions of Pd (NH$_3$)$_4$Cl$_2$ and H$_2$PtCl$_6$, respectively. These silica-supported clusters were treated in ambient air, flowing dry air, and flowing H$_2$ using the same procedures as the metal-zeolite samples.

Au clusters dispersed on SiO$_2$ (Cab-O-Sil, HS-5, 310 m$^2$ g$^{-1}$ were prepared using an Au(en)$_2$Cl$_3$ (en=ethylenediamine) complex.

Characterization of Zeolite Metal Loading and Phase Purity

LTA-encapsulated metal nanoparticle samples were synthesized with Au and Pd (Au$_n$Pd$_{100-n}$NaLTA), Au and Pt (Au$_n$Pt$_{100-n}$NaLTA), or Pd and Pt (Pd$_n$Pt$_{100-n}$NaLTA) and a broad range of molar ratios for each metal pair. The quantities of metal precursors added during the synthesis were selected to achieve total metal loadings of 1.0 wt. % in each sample, assuming complete incorporation of the added metal into the recovered solids. The nominal molar ratios of metal species are denoted by the subscripts for each sample (e.g., Au$_{67}$Pd$_{33}$NaLTA; 67 Au: 33 Pd molar ratios).

Table 1 summarizes the bimetallic samples synthesized as well as the ultimate metal content and composition of these samples, as measured by ICP. Elemental analysis confirms that actual metal loadings and compositions are similar to their nominal values in all cases, consistent with complete incorporation of the added metal species into the synthesized solids. Without being bound by any particular theory, it is believed that such complete incorporation may be attributed to the metal cations' attached ligands, which covalently anchor to solidifying silicates and preclude the solvation of metal precursors in the supernatant solution that is ultimately removed by filtration.

TABLE 1

| Sample | Wt. % Metal[a] | Metal Ratio[a] | ⟨d$_{TEM}$⟩[b] nm | DI[c] |
|---|---|---|---|---|
| AuNaLTA | 1.1 | — | 2.3 ± 0.4 | 1.09 |
| PdNaLTA | 1.0 | — | 1.6 ± 0.3 | 1.10 |
| PtNaLTA | 1.1 | — | 1.3 ± 0.3 | 1.17 |
| Au$_{67}$Pd$_{33}$NaLTA | 1.0 | 65 Au:35 Pd | 1.7 ± 0.3 | 1.09 |
| Au$_{50}$Pd$_{50}$NaLTA | 0.9 | 54 Au:46 Pd | 1.5 ± 0.3 | 1.08 |
| Au$_{33}$Pd$_{67}$NaLTA | 0.7 | 32 Au:68 Pd | 1.5 ± 0.3 | 1.11 |
| Au$_{67}$Pt$_{33}$NaLTA | 1.1 | 62 Au:38 Pt | 1.4 ± 0.3 | 1.15 |
| Au$_{50}$Pt$_{50}$NaLTA | 0.8 | 52 Au:48 Pt | 1.4 ± 0.3 | 1.09 |
| Au$_{33}$Pt$_{67}$NaLTA | 1.2 | 62 Au:38 Pt | 1.3 ± 0.2 | 1.07 |
| Pd$_{80}$Pt$_{20}$NaLTA | 1.1 | 80 Pd:20 Pt | 1.4 ± 0.3 | 1.09 |
| Pd$_{65}$Pt$_{35}$NaLTA | 1.1 | 61 Pd:39 Pt | 1.3 ± 0.2 | 1.06 |
| Pd$_{20}$Pt$_{80}$NaLTA | 1.0 | 24 Pd:76 Pt | 1.3 ± 0.2 | 1.05 |

[a]Analyzed by inductively-coupled plasma optical emission spectroscopy.
[b]Surface area weighted mean cluster diameter determined via TEM (Equation 1).
[c]Dispersity Index computed as the surface averaged cluster diameter divided by the number averaged diameter (Equation 2).

X-Ray diffractograms of the synthesized solids, collected after treatments in O$_2$ (623 K) and then H$_2$ (623 K), verified the presence of the intended LTA structures in all samples; representative diffractograms are shown in FIG. 1. Zeolite crystallinities were greater than 95% for each sample, as determined from the integrated areas of the three most intense Bragg lines, using metal-free NaLTA as a standard. Diffraction lines for bulk metal phases (Au, Pd, or Pt) were absent from these samples, and their crystallinity was unchanged by treatments in air or H$_2$ at elevated temperature (823 K). Thus, it can be concluded that the synthesized zeolites are crystalline, thermally-stable, and free of large metal crystallites (>10 nm), which would have exhibited their characteristic Bragg lines in the diffractograms.

Assessment of Encapsulated Metal Cluster Size Distributions and Thermal Stability TEM micrographs were used to assess the size, location, and thermal stability of metal structures formed by hydrothermal synthesis and post synthetic air and $H_2$ treatments of the crystallized zeolites. Previous studies have shown that these synthetic protocols, implemented with only a single metal (Au, Pd, or Pt), lead to highly dispersed monometallic clusters free of synthetic debris and located predominantly within the zeolite voids. Clusters form in these zeolites as a result of the $H_2$ treatment, during which isolated metal cations are reduced and subsequently migrate throughout the framework to form agglomerates; the ultimate size of these agglomerates is dictated by the mobility of the metal atoms during this critical reduction step, with greater mobility (e.g. as a result of higher treatment temperature) leading to larger nanoparticles. FIGS. 2A-2F show TEM micrographs and particle size distributions for these monometallic clusters, as well as a selection of the bimetallic samples considered in this study. The total metal content in each sample is 1 wt. %. Table 1 also summarizes the TEM-derived surface-averaged cluster diameters ($\langle d_{TEM} \rangle$; Equation 1) and dispersity indices (DI; Equation 2) for each of the synthesized $Au_nPd_{100-n}$NaLTA, $Au_nPt_{100-n}$NaLTA, and $Pd_nPt_{100-n}$NaLTA samples.

The surface-averaged cluster diameter of monometallic samples (AuNaLTA: 2.3 nm, PdNaLTA: 1.6 nm, PtNaLTA: 1.3 nm; Table 1) varies inversely with the Tammann temperature of the embedded metal (Au: 668 K, Pd: 914 K, Pt: 1022 K), consistent with the formation of relatively larger clusters by metals with greater mobility. Bimetallic samples gave surface-averaged cluster sizes (e.g. $Au_{50}Pd_{50}$NaLTA: 1.5 nm, $Au_{50}Pt_{50}$NaLTA: 1.4 nm, and $Pd_{65}Pt_{35}$NaLTA: 1.3 nm; Table 1) similar to their most stable single-metal counterparts (i.e., the metal with the higher Tammann temperature), and exhibited cluster size distributions that were both monodisperse (DI: 1.05-1.15; Table 1) and unimodal (FIGS. 2A-2F). The addition of Pd to Au, Pt to Au, and Pt to Pd leads to smaller nanoparticle sizes relative to monometallic Au or Pd, consistent with inhibited cluster growth processes brought forth by the addition of a second metal with higher Tammann temperature. Such enhancements in the metal cluster stability generally vary in a highly non-linear fashion with composition; consequently, even bimetallic samples with relatively high Au content (e.g., $Au_{67}Pd_{33}$: 1.7 nm, $Au_{67}Pt_{33}$: 1.4 nm) exhibited cluster diameters disproportionately smaller than monometallic AuNaLTA (2.3 nm). The nearly monodisperse size distributions in these bimetallic samples implies that their clusters are uniformly distributed in composition; nominally bimetallic clusters that are heterogeneously distributed in composition, by contrast, would typically show a broad range of cluster sizes because of the differing thermal stabilities of their constituent metals. Mixtures of two types of monometallic clusters in a given same sample, for instance, are expected to exhibit bimodal size distributions with poor monodispersity (i.e., DI>1.5), and surface-averaged cluster diameters that reflect the composition-weighted mean value of the corresponding monometallic samples. The small cluster diameters and monodisperse size distributions of the LTA-encapsulated bimetallic samples therefore suggest the predominant presence of alloy nanoparticles.

Figure 3:
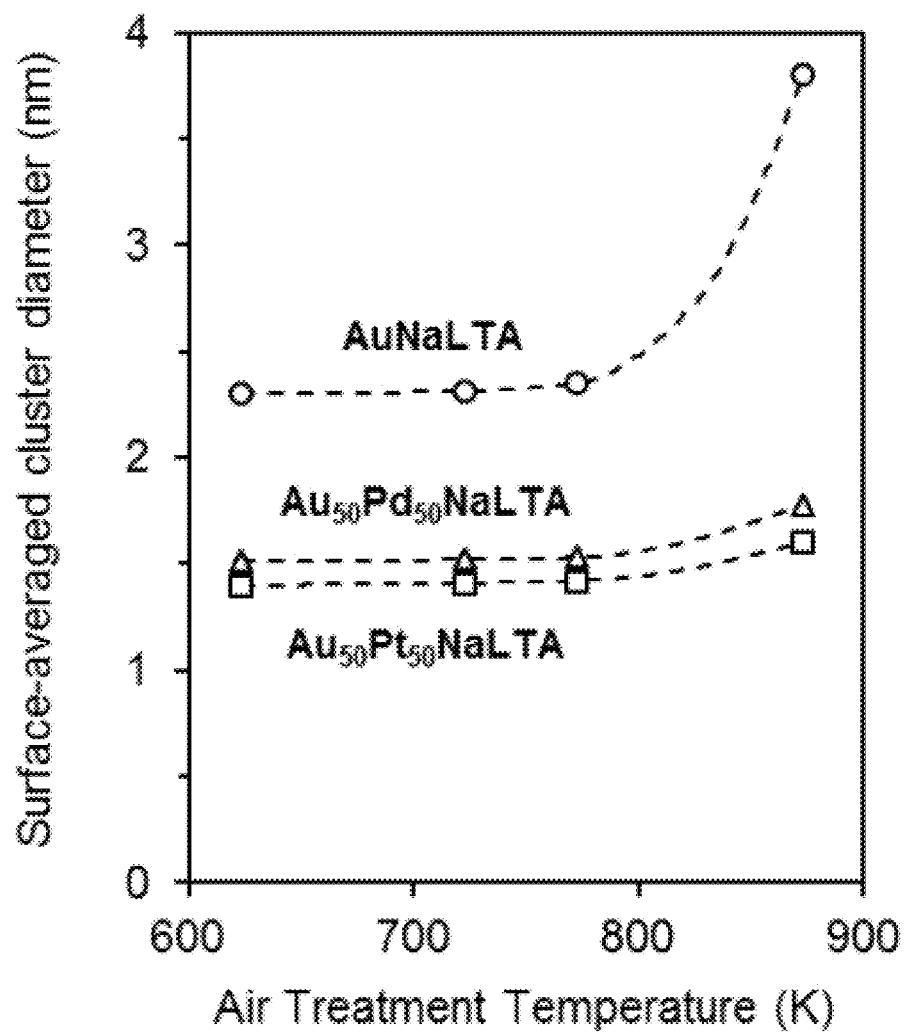
FIG. 3 shows the effect of flowing dry air treatment temperature (1.67 $cm^3$ $g^{-1}$ $s^{-1}$, 5 h) on the TEM-derived surface-averaged cluster diameter ($\langle d_{TEM} \rangle$) of metal particles in AuNaLTA (o), $Au_{50}Pd_{50}$NaLTA (Δ), and $Au_{50}Pt_{50}$NaLTA (□).

The stability of monometallic Au and Au-bimetallic clusters was examined and compared during treatment in flowing air by heating to final temperatures between 623 and 873 K (0.033 K s$^{-1}$) and holding for 5 h. Previous studies of LTA-encapsulated Pt and Pd clusters revealed that the confining environment of the zeolite frameworks entirely precludes agglomeration of these metals in air up to 873 K, while monometallic Au clusters retain their size to approximately 823 K (see, M. Choi et al., *J. Am. Chem. Soc.* 2010, 132, 9129-9137; and T. Otto et al., *J. Catal.* 2016, 339, 195-208). The TEM-derived surface-averaged cluster diameters ($\langle d_{TEM} \rangle$; Equation 1) of AuNaLTA, $Au_{50}Pd_{50}$NaLTA, and $Au_{50}Pt_{50}$NaLTA are shown in FIG. 3 as a function of the final air treatment temperature. Cluster diameters of all samples (AuNaLTA: 2.3 nm, $Au_{50}Pd_{50}$NaLTA: 1.5 nm, $Au_{50}Pt_{50}$NaLTA: 1.4 nm) were unchanged by treatment at or below 773 K, though the monometallic Au clusters increased in size by 65% (to 3.8 nm) after treatment at 873 K. The alloyed clusters, by contrast, increased only slightly in size after treatment at 873 K; clusters in $Au_{50}Pd_{50}$NaLTA increased in size by 20% to 1.8 nm, and those in $Au_{50}Pt_{50}$NaLTA increased by 14% to 1.6 nm. The dispersity index (DI) values (Equation 2) of these samples also increased as a result of this treatment at 873 K. The DI of clusters in AuNaLTA rose significantly from 1.07 to 1.62, while the bimetallic clusters exhibited much smaller increases ($Au_{50}Pd_{50}$NaLTA: 1.09 to 1.23, $Au_{50}Pt_{50}$NaLTA: 1.09 to 1.17) and thus remained relatively monodisperse (DI<1.5). It is concluded that the admixture of Au with Pd or Pt, with higher Tamman temperatures, acts to decrease the mobility and thus stabilize Au species, conferring dramatic improvements in cluster stability compared to monometallic Au. These clusters benefit from resistance to thermal sintering as a result of this alloying effect in addition to the strong cluster stabilization provided by the zeolite framework, which renders encapsulated clusters significantly more resistant to agglomeration than those dispersed on mesoporous supports.

UV-Visible Evidence for Intracluster Metal Mixing in AuPd and AuPt Bimetallics

UV-vis spectra of AuNaLTA, $Au_nPd_{100-n}$NaLTA, and $Au_nPt_{100-n}$NaLTA were used to confirm the absence of monometallic Au clusters in the crystallized and reduced bimetallic samples. Such monometallic Au clusters, as well as core-shell bimetallic structures with pure Au on the surface, would exhibit localized surface plasmon resonance (LSPR) absorption bands in the range 500-600 nm. Monometallic Pt and Pd clusters or Au-bimetallic clusters, by contrast, show no distinguishing absorption features in the UV-visible range. The presence of an LSPR band thus serves as a diagnostic for Au clusters greater than 2 nm in diameter, the minimum particle size at which Au exhibits plasmon resonance.

Figure 4A:
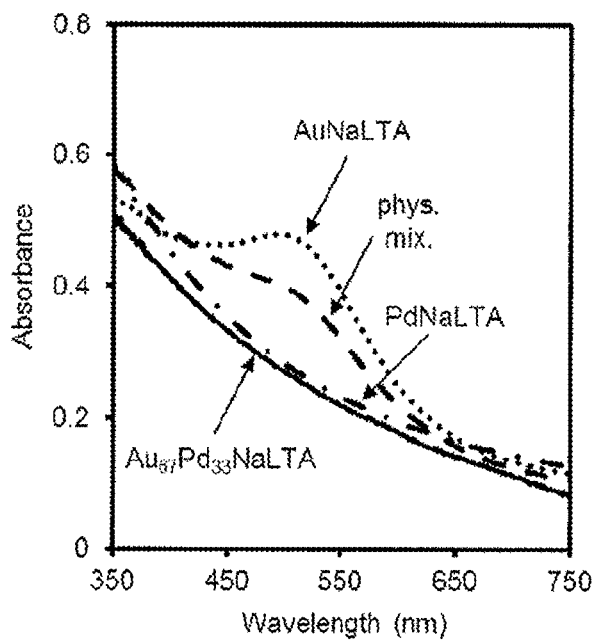
FIGS. 4A and 4B both show the UV-visible absorption spectra of monometallic AuNaLTA (•••), monometallic PdNaLTA (4A) or PtNaLTA (4B) (-•-), a physical mixture of monometallic AuNaLTA and PdNaLTA (4A) or PtNaLTA (4B) (---), and bimetallic $Au_{67}Pd_{33}$NaLTA (4A) or $Au_{67}Pt_{33}$NaLTA (4B) (solid line).
Figure 4B:
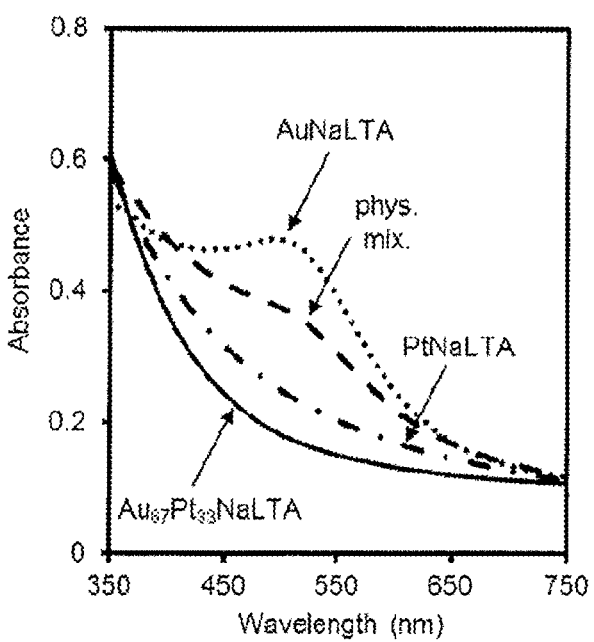
Figure 6A:
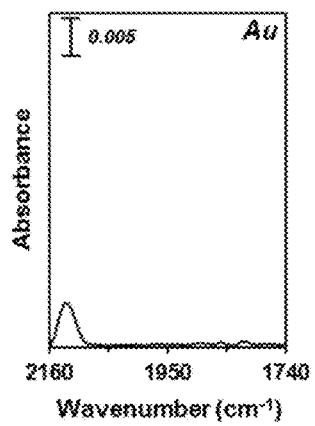
FIGS. 6A-6E show the IR spectra of CO adsorbed on monometallic or bimetallic $Au_nPd_{100-n}$CaLTA samples (1 kPa CO, 99 kPa He) at 278 K after H2 treatment (573 K, 20 kPa H2, 80 kPa He) (gray spectra) and after heating in CO (1 kPa CO, 99 kPa He) up to 353 K (black spectra).
Figure 6B:
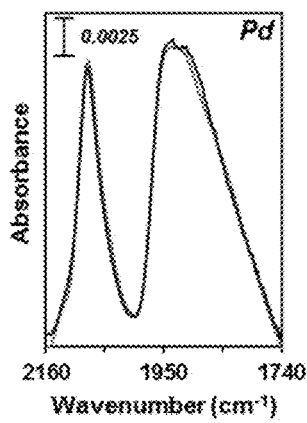
Figure 6C:
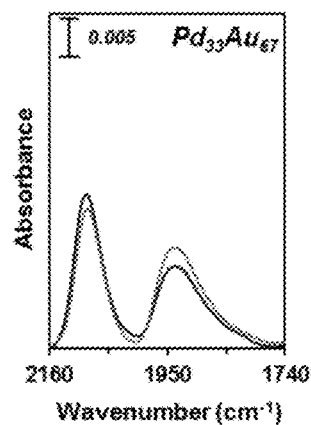
Figure 6D:
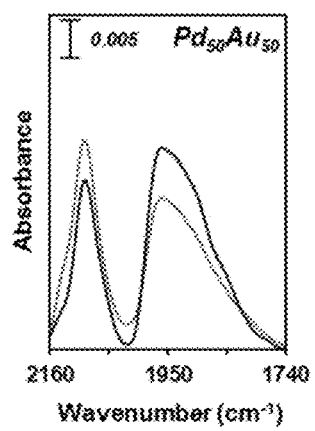
Figure 6E:
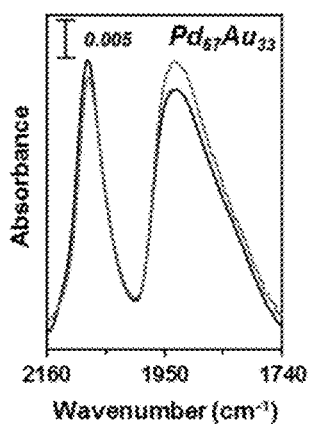

UV-visible spectra of AuNaLTA, $Au_{67}Pd_{33}$NaLTA, $Au_{67}Pt_{33}$NaLTA, and 2:1 physical mixtures (by moles of metal) of AuNaLTA and PtNaLTA or AuNaLTA and PdNaLTA are shown in FIGS. 4A and 4B.

AuNaLTA samples and physical mixtures of monometallic AuNaLTA and PdNaLTA or AuNaLTA and PtNaLTA each showed an LSPR absorption band, consistent with the presence of monometallic Au clusters greater than 2 nm in diameter ($\langle d_{TEM} \rangle$ =2.3 nm; FIGS. 2A-2F) in each sample. The absorption wavelength of these plasmon bands (~506 nm) is characteristic of Au nanoparticles smaller than 5 nm in diameter, but is insensitive to cluster size below this threshold. The bimetallic and monometallic Pd and Pt samples, by contrast, exhibited only indefinite background features in the relevant range for plasmon resonance (500-600 nm), rather than distinct absorption bands indicative of monometallic Au. Pd or Pt can contribute slightly to diffuse background absorption in the visible range; consequently, the slight differences in the background absorption of the UV-Vis spectra, which are blanked with metal-free NaLTA, can be attributed to differing contents of these metals in each sample. The lack of LSPR band features in $Au_{67}Pd_{33}NaLTA$ and $Au_{67}Pt_{33}NaLTA$ confirms the substantive absence of monometallic Au clusters ≥2 nm in diameter, even though ICP analysis confirms the presence of Au in a 2:1 molar ratio with Pt or Pd (Table 1). Au-bimetallic samples with lower Au content (i.e., Au/Pd=1, Au/Pd=0.5, Au/Pt=1, and Au/Pt=0.5) similarly lacked LSPR absorption bands. These spectra are therefore consistent with bimetallic clusters that are homogeneously distributed in composition, even when enriched with less stable Au metal. The surface-averaged cluster diameters of $Au_{67}Pd_{33}NaLTA$ (1.7 nm) and $Au_{67}Pt_{33}NaLTA$ (1.4 nm), however, are near the lower size limit for plasmon resonance (2 nm); only 7% and 2% of the clusters in these samples, respectively, are at or above this limit. Monometallic Au clusters, if present in the bimetallics, are expected to preferentially comprise these larger nanoparticles because of the relatively low Tammann temperature of Au, though it is unclear whether such small concentrations would have been evident in UV-Vis spectra via LSPR absorption. It is therefore concluded that the absence of LSPR bands in Au-bimetallic samples is consistent with small cluster sizes and metal alloying, but cannot independently confirm this alloying.

Infrared Evidence for Metal Alloying and Intracluster Metal Atom Mobility Upon CO Binding The arrangement of atoms in bimetallic clusters is often understood and categorized in the context of core-shell structures, intimately mixed intermetallic phases with ordered binding arrangements, or random intracluster distributions of each metal species. These specific structures, however, are rarely preserved in practice because alloy clusters undergo dynamic restructuring in response to changes in their environment, including the binding of adsorbates, temperature changes, or metal-support interactions. Here, the aim is to induce this restructuring in zeolite-encapsulated bimetallic clusters by exposing them to CO. Infrared (IR) spectra of the adsorbed CO are used to deduce the surface compositions of bimetallic clusters and to probe any changes in surface compositions that result from intracluster restructuring.

IR spectra of CO adsorbed on metal clusters were collected for monometallic and bimetallic samples synthesized and prepared as described herein above; the NaLTA host zeolites (0.42 nm apertures) were exchanged with $Ca^{2+}$ to form CaLTA (0.50 nm apertures) before these measurements in order to improve the accessibility of CO to encapsulated metal clusters. $Au_nPd_{100-n}CaLTA$ and $Au_nPt_{100-n}CaLTA$ bimetallic samples were first treated in H2 (20 kPa) at 573 K for 1 h before cooling to sub-ambient temperature (278 K and 263 K, respectively) in He (100 kPa). This heating procedure favors the enrichment of bimetallic cluster surfaces with the lower surface energy component, in both cases Au, which tends to diffuse to the surface in order to minimize the total Gibbs free energy of the nanoparticles. The cooled samples were then exposed to CO (1.0 kPa) and IR spectra were collected. Such spectra are predicted to reflect CO adsorption onto bimetallic surfaces enriched with Au. Each sample was next heated to 353 K under 1.0 kPa CO for 0.5 h and cooled back to 278 K or 263 K for the collection of a second spectrum. This heating with exposure to CO is intended to draw Pt or Pd atoms to the surface, thus decreasing the Au surface concentration of the clusters and leading to an apparent hysteresis effect when the second absorption spectrum is collected. Such intracluster rearrangement is driven by the higher binding energy of CO on Pt (atop: 136 kJ mol$^{-1}$) or Pd (atop: 94 kJ mol$^{-1}$; bridged: 146 kJ mol$^{-1}$) relative to Au (atop: 50 kJ mol$^{-1}$), which favors the displacement of surface Au atoms by the more strongly binding metal to decrease the cluster free energy. The mild heating to 353 K was applied to increase the rate of intracluster metal diffusion and more rapidly induce this restructuring. Clear differences in the CO IR absorption before and after this intermittent heating in CO thus provide evidence that the clusters in $Au_nPd_{100-n}CaLTA$ and $Au_nPt_{100-n}CaLTA$ are indeed bimetallic. The magnitude of the hysteresis effect is expected to be small for $Pd_nPt_{100-n}CaLTA$ samples, because differences in CO binding energies on Pd and Pt are relatively minor. Metal alloying in these samples was instead assessed using CO IR spectra collected for a wide variety of metal compositions and also using EXAFS analysis.

IR spectra of CO adsorbed on 1 wt. % (total metal) $Au_nPt_{100-n}CaLTA$ samples (for n=0, 33, 50, 67, and 100), measured under 1.0 kPa CO at 263 K before and after intermittent heating in CO at 353 K, are shown in FIGS. 5A-5B. Monometallic Au (FIG. 5A) and Pt (FIG. 5B) samples exhibit absorption bands at 2120 cm$^{-1}$ and 2070 cm$^{-1}$ respectively, which correspond to atop adsorption of CO on Au and Pt. CO bridged bonding absorption bands on Pt (1800-1900 cm$^{-1}$) are weak and undiscernible. The integrated intensity of the Pt—CO band in PtCaLTA is greater than that of the Au—CO band in AuCaLTA by a factor of 18. This difference in the integrated band areas reflects the relatively high intensity of Pt—CO bands (via high absorption cross-section) and the slightly higher density of surface metal atoms in PtCaLTA (0.005 $mol_{surf-Pt}g^{-1}$) compared to AuCaLTA (0.003 $mol_{surf-Au}g^{-1}$). Pt—CO bands, evident in each bimetallic sample spectrum, FIGS. 5C-5E, increase monotonically in intensity with increasing Pt content, consistent with increasing concentrations of surface Pt atoms. A distinct Au—CO band is visible in the Au-rich bimetallic sample ($Au_{67}Pt_{33}CaLTA$), but becomes muddled or indistinguishable at lower Au/Pt ratios. This weakening of the Au—CO band intensity can be attributed to the decreasing overall Au content, the relatively small intensity of Au—CO bands relative to Pt—CO, and the preferential adsorption of CO onto more strongly binding Pt atoms in bimetallic clusters. Each of these contributing effects to the decreasing Au—CO band intensity is expected to become more dramatic as the Pt/Au ratio increases, and together lead to the near complete disappearance of the Au—CO band when Pt/Au=2. Intermittent heat treatment of the Pt—Au bimetallics in CO at 353 K leads to significant hysteresis in the IR absorbance for each of the bimetallic samples, while the IR spectra for monometallic Pt and Au samples remain unchanged by this treatment. This intervening thermal treatment leads to increases in the intensity of the Pt—CO bands in the alloy samples, consistent with the displacement of surface Au atoms by more strongly CO-binding Pt atoms. The fractional increase in the Pt—CO band intensity caused by this restructuring decreases monotonically with increasing Pt to Au molar ratios (fractional increases of 20%, 15% and 9% for Pt/Au=0.5, 1, and 2, respectively). This trend is consistent with the expectation that samples with relatively more Pt-rich clusters should undergo less dramatic fractional changes in their Pt surface concentration during restructuring. These data, taken together, show compelling evidence of intracluster restructuring and are consistent with the predominant presence of alloy nanoparticles within the AuPt bimetallic samples.

Figure 7:
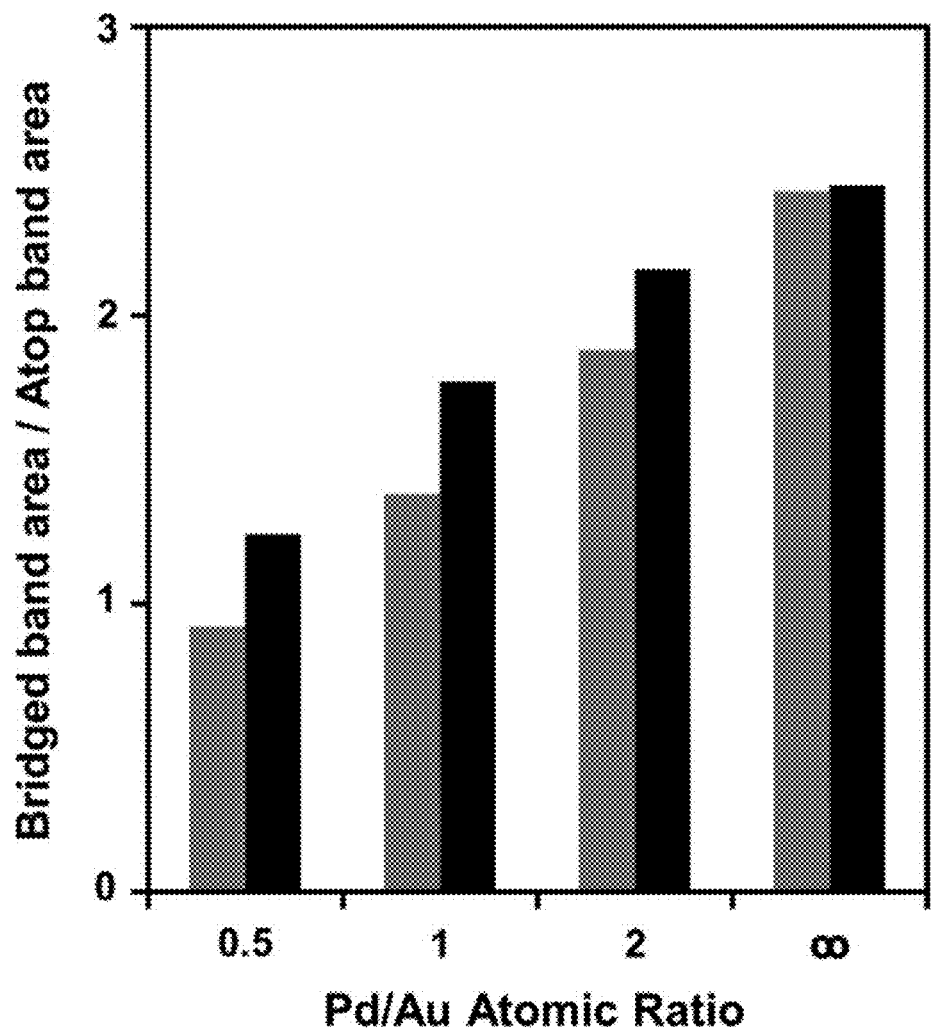
FIG. 7 shows ratios of the integrated intensities of the Pd—CO (bridged) IR absorption bands to the Pd—CO (atop) bands as a function of Pd/Au atomic ratio in AuPd-CaLTA bimetallic samples.

IR spectra of CO adsorbed on 1 wt. % (total metal) $Au_nPd_{100-n}$CaLTA samples (for n=0, 33, 50, 67, and 100), measured under 1.0 kPa CO at 278 K before and after intermittent heating in CO at 353 K, are shown in FIGS. 6A-6E. AuCaLTA (FIG. 6A) shows a weak absorption band at 2130 $cm^{-1}$ corresponding to atop adsorption of CO on Au, while PdCaLTA (FIG. 6B) exhibits significantly more intense absorption bands at 2090 $cm^{-1}$ and 1930 $cm^{-1}$, which can be assigned to atop binding and ridged (vicinal) binding of CO onto Pd, respectively. The relatively weak intensity of the Au—CO band likely results from the incomplete coverage of Au surfaces at the conditions of the measurement and the small absorption cross section of CO on Au surfaces. Atop and bridged Pd—CO bands are present in each bimetallic sample spectra, while Au—CO bands are not clearly distinguishable. The poor intensity and resolution of these Au—CO bands in the bimetallic samples may result from the preferred adsorption of CO onto more strongly binding Pd atoms in bimetallic clusters, or the partial overlap of these Au—CO bands with much more intense atop Pd—CO bands. The intensity of the Pd—CO bands increase monotonically with the Pd/Au ratio (FIGS. 6C-6E), consistent with increasing concentrations of surface Pd atoms as the total Pd content increases. The ratio of the integrated intensity (I) of the bridged Pd—CO band to that of the atop Pd—CO band (defined as $\Box=I_{bridge}/I_{atop}$) also increases monotonically with the Pd to Au molar ratio. See FIG. 7. $\Box$ values measured before intermittent heating in CO were 0.9, 1.4, 1.9, and 2.4 for Pd/Au=0.5, 1, 2, and ∞, respectively; α values measured after heating in CO similarly approached the value for pure Pd clusters, but were slightly larger in magnitude. This increasing preference for bridged CO binding on Pd reflects the decreasing concentration of surface Au atoms, which can dilute Pd atom domains on bimetallic clusters and decrease the fraction of vicinal Pd atoms required for bridged CO binding. Mixtures of monometallic Au and Pd clusters, in contrast, would be expected to maintain constant $\Box$ values with increasing Pd/Au ratios because of the absence of Pd surface dilution by Au. Heating of the bimetallic samples in CO at 353 K leads to changes in the IR absorption spectra, while the spectra of monometallic samples are unaffected by the same treatment. This treatment in CO leads to greater bridged Pd—CO band intensities for each bimetallic sample, consistent with increased fractions of vicinal Pd atoms brought forth by Pd migration to the cluster surfaces. Atop Pd—CO bands also decrease slightly in intensity following this treatment, which reflects the preference of CO molecules linearly bound on isolated Pd atoms to adopt more stable bridged bonding configurations when vicinal binding sites become available. These trends in the absorption spectra are therefore consistent with cluster alloying and suggest the absence of monometallic clusters in AuPd bimetallic samples.

The relatively facile restructuring observed for AuPt and AuPd clusters suggests that the bimetallic surfaces are free of strongly bound sulfur contaminants derived from the protecting ligands used in the synthesis. Such contaminants would tend to anchor to Pt or Pd surface atoms because of the high bond energies of Pt—S (233 kJ $mol^{-1}$) and Pd—S (183 kJ $mol^{-1}$) relative to Au—S (126 kJ $mol^{-1}$). These surface-bound sulfur species, if present, would have led to diffuse Pt—CO and Pd—CO bands and also precluded intracluster restructuring because of their higher binding energies relative to CO. The apparent cleanliness of the metal surfaces is consistent with previous chemisorption and CO IR studies of LTA-encapsulated monometallic Pt, Pd, and Au clusters, which were shown to be free of contaminant species and rendered fully accessible after the post-synthetic air (623 K) and $H_2$ (623 K) treatments applied as described herein.

Figure 8:
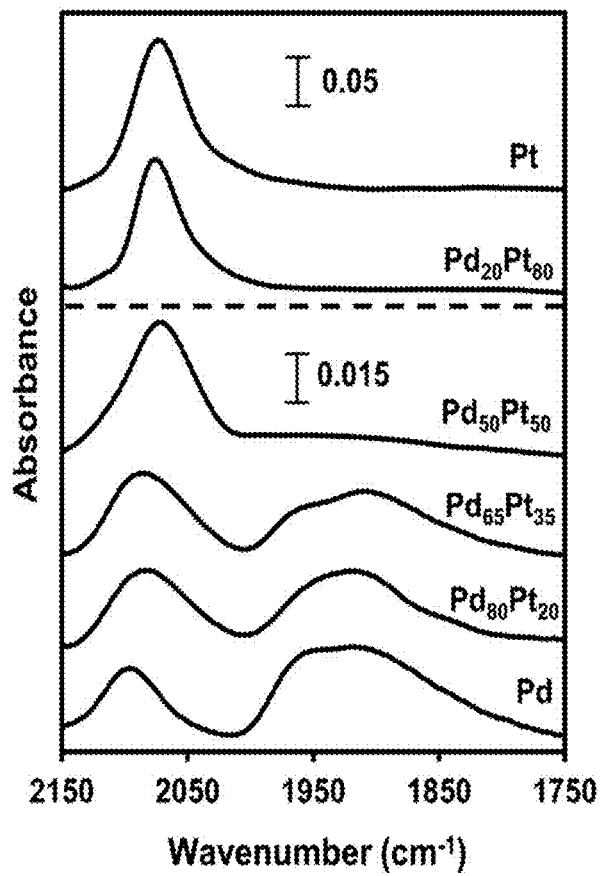
FIG. 8 shows the IR spectra of CO adsorbed on monometallic or bimetallic $Pd_nPt_{100-n}$CaLTA samples (1 kPa CO, 99 kPa He) at 313 K after H2 treatment (573 K, 20 kPa H2, 80 kPa He).
Figure 9:
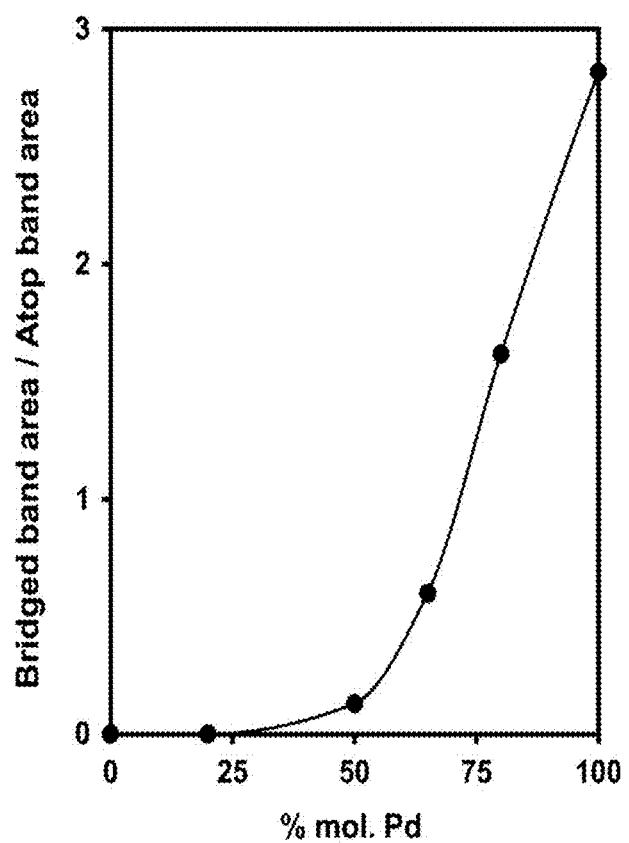
FIG. 9 shows the ratio of the integrated intensity of the Pd—CO (bridged) absorption band (~1900 $cm^{-1}$) to that of the metal-CO atop band (~2100 $cm^{-1}$) as a function of Pd content in $Pd_nPt_{100-n}$CaLTA samples.

FIG. 8 shows IR spectra of CO adsorbed on metal clusters in $Pd_nPt_{100-n}$CaLTA samples (for n=100, 80, 65, 50, 20, and 0) at 313 K under 1 kPa CO. The absorption spectra of CO on monometallic Pt and Pd samples at 313 K closely resemble those collected at slightly lower temperatures (Pt—CO: 263 K, FIG. 5; Pd—CO: 278 K, FIG. 6). PtCaLTA exhibits an intense absorption band at 2070 $cm^{-1}$ associated with atop CO adsorption, and monometallic Pd shows absorption bands at 2090 $cm^{-1}$ and 1930 $cm^{-1}$, corresponding to atop and bridged CO binding, respectively. The addition of Pt to Pd leads to monotonic increases in the integrated intensity of the linearly bonded CO band and concomitant decreases in the bridged Pd—CO band. The ratio of the integrated intensities for these bands as a function of Pd content is shown in FIG. 9. The increasing intensity of the atop CO band with the Pt/Pd ratio is consistent with increasing concentrations of Pt—CO surface complexes, which exhibit characteristically high IR absorption intensity. The accompanying decline in the Pd—CO bridged band intensity is an expected consequence of the decreasing Pd content of these samples, but may further result from the dilution of Pd surfaces with Pt, which would decrease the fraction of vicinal Pd atoms required for bridged bonding. This surface dilution requires metal alloying and cannot take effect in samples consisting of mixtures of monometallic metal clusters; consequently, the ratio of bridged to atop absorption in such mixtures is expected to decline monotonically with Pd content, reaching a value of zero only when there is no Pd remaining in the sample. The ratio of bridged to atop absorption bands for alloy clusters, by contrast, is expected to reach a value of zero once the Pd surfaces have been sufficiently diluted with Pt to preclude vicinal CO binding to Pd, at which point the remaining surface Pd atoms will exclusively bind CO in an atop configuration. The trend in FIG. 9 shows that that the ratio of bridged to atop absorption band intensities reaches a value of zero between 20-50 mol % Pd, suggesting the absence of monometallic Pd clusters and the complete isolation of surface Pd atoms by surrounding Pt domains. These data are therefore consistent with metal alloying in the $Pd_nPt_{100-n}$CaLTA samples.

Assessment of Metal Cluster Size and Composition with EXAFS Analysis

Figure 10:
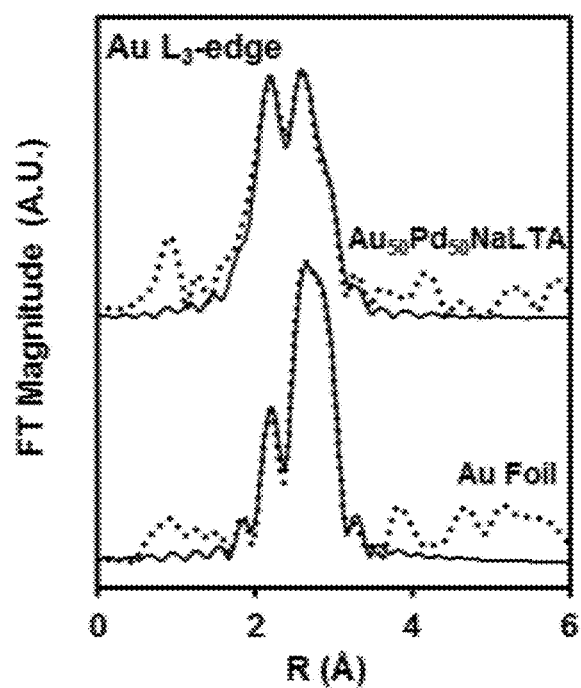
FIG. 10 shows Fourier transforms (FT) of the $k^3$-weighted extended X-ray absorption fine structure (EXAFS) and their corresponding single scattering fits for $Au_nPd_{100-n}$NaLTA and Au foil measured at the Au-$L_3$ edge. Dotted lines represent experimental data, while solid lines represent fitted data.
Figure 11:
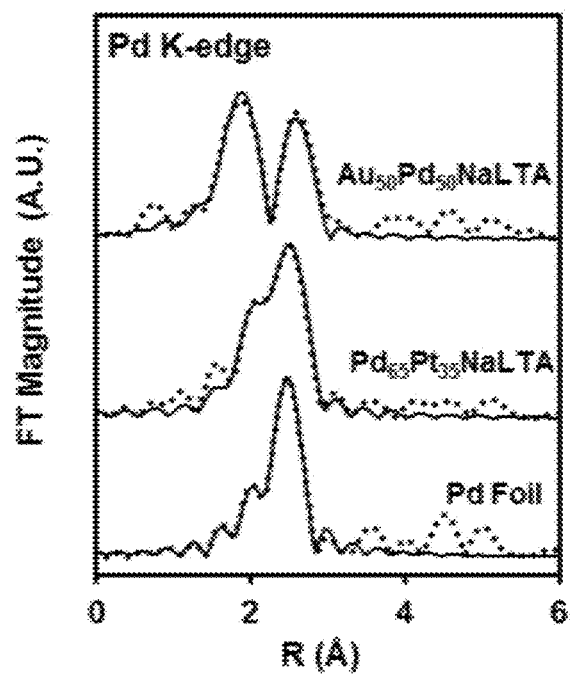
FIG. 11 shows Fourier transforms of the $k^3$-weighted EXAFS and their corresponding single scattering fits for $Au_{50}Pd_{50}$NaLTA, $Pd_{65}Pt_{35}$NaLTA, and Pd foil measured at the Pd—K edge. Dotted lines represent experimental data, while solid lines represent fitted data.
Figure 12:
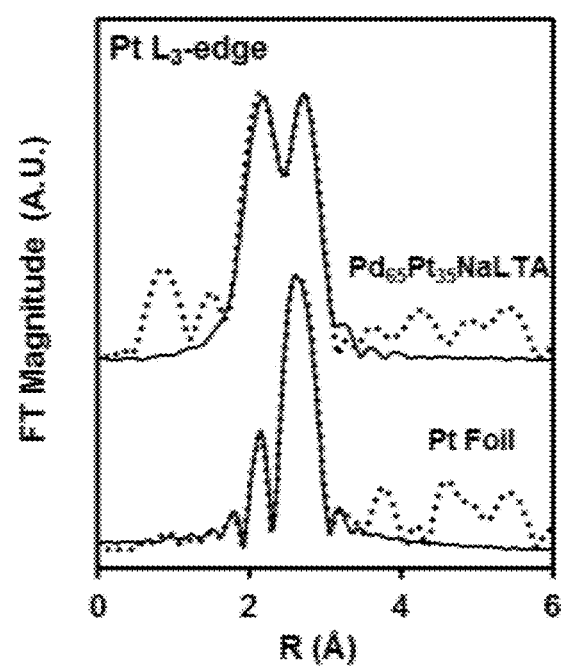
FIG. 12 shows Fourier transforms of the $k^3$-weighted EXAFS and their corresponding single scattering fits for $Pd_{65}Pt_{35}$NaLTA and Pt foil measured at the Pt-$L_3$ edge. Dotted lines represent experimental data, while solid lines represent fitted data.

Fourier transforms of the $k^3$-weighted EXAFS and their corresponding fits for bimetallic samples and reference foils measured at the Au-$L_3$, Pd—K, and Pt-$L_3$ edges are shown in FIGS. 10, 11, and 12, respectively. X-ray absorption spectra presented in FIGS. 10-12 were collected at ambient temperature under 100 kPa Ar following $H_2$ treatment (573 K, 10 kPa $H_2$, 90 kPa He).

Metal coordination numbers (N), interatomic distances (D), and Debye-Waller factors ($\sigma^2$) obtained from these single scattering fits are shown in Table 2 below. Values in parentheses indicate the error in the final digit.

TABLE 2

| Sample | Edge | Scatterer | N[a] | D[b], Å | $\sigma^{2[c]}$, Å$^2$ |
|---|---|---|---|---|---|
| Au$_{50}$Pd$_{50}$NaLTA | Au-L$_3$ | Au | 6 (1)[d] | 2.73 (2) | 0.011 (4) |
| | | Pd | 3.2 (8) | 2.73 (1) | 0.008 (2) |
| | Pd—K | Au | 5 (1) | 2.73 (1) | 0.008 (2) |
| | | Pd | 3.1 (7) | 2.69 (1) | 0.007 (1) |
| Au$_{65}$Pt$_{35}$NaLTA | Pd—K | Pd | 4.4 (4) | 2.74 (1) | 0.008 (1) |
| | | Pt | 4.0 (3) | 2.73 (1) | 0.008 (1) |
| | Pt-L$_3$ | Pd | 4 (1) | 2.73 (1) | 0.008 (1) |
| | | Pt | 5 (1) | 2.72 (1) | 0.008 (1) |

FIG. 10 shows the Fourier transform amplitudes and corresponding fits of the EXAFS oscillations at the Au-L$_3$ edge for Au$_{50}$Pd$_{50}$NaLTA and the Au foil. Fits of the Au-L$_3$ EXAFS for Au$_{50}$Pd$_{50}$NaLTA confirm two unique coordination shells around Au: one Au shell with a coordination number of 6±1 and interatomic distance 2.73±0.02 Å, and one Pd shell with coordination number 3.2±0.8 and interatomic distance 2.73±0.01 Å (Table 2). These individual coordination shells thus lead to a total Au coordination number of 9±1 after applying the propagation of uncertainty and rounding for significant digits. This total coordination number is significantly lower than that of bulk Au or AuPd alloys (12), indicating the prevalence of coordinatively unsaturated metal clusters. The interatomic distance (2.73 Å) derived from the fit is also smaller than that of a bulk Au$_{50}$Pd$_{50}$ alloy (~2.81 Å), consistent with the tendency for interatomic distances to contract in highly dispersed clusters. The total coordination number derived from the fit corresponds to metal clusters 1.3-2.1 nm in diameter assuming that they adopt FCC cuboctahedral structures; this diameter is consistent with that measured by TEM (1.6 nm) (Table 1). These data are consistent with the presence of alloyed phases and highly dispersed clusters, but must be considered concurrently with equivalent measurements at the Pd—K edge to provide a holistic interpretation of the metal coordination.

Fourier transform amplitudes and fits of the EXAFS oscillations at the Pd—K edge for Au$_{50}$Pd$_{50}$NaLTA and Pd foil are shown in FIG. 11. Structural parameters derived from these fits (Table 2) showed two coordination shells around Pd absorbers: a Pd shell with coordination number 3.1±0.7 and interatomic distance 2.69±0.01 Å, and an Au shell with coordination number 5±1 and interatomic distance 2.73±0.01 Å. These individual coordination shells give a total Pd coordination number of 8±1. The addition of light scatterers (O or S) did not lead to improvements in the fit, consistent with the exclusive presence of metallic phases. The total coordination number and Au—Pd coordination number derived from these fits at the Pd—K edge are identical to or within error of equivalent parameters originating from the Au-L$_3$ EXAFS. The close agreement in the total Pd and Au coordination numbers suggests that Pd and Au atoms have similar first surroundings and occupy clusters of the same size, consistent with intimate metal mixing and the substantive absence of segregated metal phases. Randomly mixed alloy clusters with the experimentally measured Pd/Au ratio (Pd/Au=1; Table 1) and the fitted total coordination number (9) would be expected to give Au—Au, Pd—Pd, and Au—Pd coordination numbers of ~4.5 each. The mean Au—Pd coordination number (4±1) falls within error of this value, suggesting uniform intracluster distributions of metal atoms. Therefore, it is concluded that the Au surface enrichment brought forth by the H$_2$ pretreatment of these samples at 353 K was lost during the ~10 h induction period in which the samples were stored at room temperature under inert gas prior to XAS measurements. Such restructuring to well-mixed alloy clusters did not occur prior to CO IR studies, likely because of the rapid cooling (−0.17 K s$^{−1}$) of the samples after treatment at 573 K to sub-ambient temperature (278 K). Au—Au and Pd—Pd coordination numbers (6±1 and 3.2±0.8, respectively) deviated slightly from the coordination number expected from random mixing (~4.5), though these values are within error of the average Au—Pd coordination number (4±1). The precision of these parameters therefore precludes speculation as to the precise intracluster distribution of metal species or their preferred occupancy on specific surface sites (e.g., corners, terraces). These parameters derived from the EXAFS, however, are consistent at each metal edge and confirm the small size, intimate metal mixing, and absence of monometallic phases in Au$_{50}$Pd$_{50}$NaLTA.

FIG. 11 shows the Fourier transform amplitudes and fits of the EXAFS at the Pd—K edge of Pd$_{65}$Pt$_{35}$NaLTA; structural parameters derived from these fits are shown in Table 2. The Pd absorbers showed Pd and Pt coordination shells with coordination numbers 4.4±0.4 and 4.0±0.3 and interatomic distances of 2.74±0.01 Å and 2.73±0.01 Å, respectively. These coordination shells lead to a total Pd atom coordination of 8.4±0.5, corresponding to 1.1-1.7 nm clusters assuming FCC cuboctahedral particles. This size is in good agreement with that determined from TEM (1.2 nm, Table 2). The inclusion of O and S scatterers did not improve the fit, suggesting the presence of only metallic phases. FIG. 12 shows the corresponding Fourier transform amplitudes and fits of the EXAFS at the Pt-L$_3$ edge of Pd$_{65}$Pt$_{35}$NaLTA. Structural parameters extracted from the fit (Table 2) gave two coordination shells around Pt: a Pd shell with coordination number 4±1 and interatomic distance 2.73±0.01 Å, and a Pt shell with coordination number 5±1 and interatomic distance 2.72±0.01 Å, leading to a total coordination number of 9±1. The total coordination number extracted from these fits of the Pt-L$_3$ EXAFS is within error of that derived from the Pd—K edge of Pd$_{65}$P$_{35}$NaLTA (8.4±0.5). This close agreement in the total coordination numbers indicates that the Pd and Pt atoms occupy clusters of the same size and have similar coordination environments, consistent with the predominant presence of these metals in alloy clusters and the absence of monometallic phases. Randomly mixed PdPt alloy clusters with the experimentally measured Pd/Pt ratio (1.56, Table 1) and the average total coordination number (9±1) are predicted to give Pd—Pd, Pd—Pt, Pt—Pd, and Pt—Pt coordination numbers of 5, 4, 5, and 4, respectively. The Pd—Pt and Pt—Pd coordination numbers derived from the EXAFS fits are within error of these predicted values, suggesting relatively uniform intracluster distributions of metal atoms. The fitted Pd—Pd and Pt—Pt coordination numbers (4.4±0.4 and 5±0.4, respectively) are also similar to the values expected from random intracluster distributions of metal atoms. Monte Carlo simulations of bimetallic PdPt clusters indicate that Pd atoms should preferentially occupy low coordination surface sites (e.g., corners, edges) at the conditions of these XAS measurements, though it is unclear from the extracted coordination numbers whether the zeolite-encapsulated clusters also adopt this configuration. The coordination numbers derived from the EXAFS of Pd$_{65}$Pt$_{35}$NaLTA, however, show internal consistency at the Pd—K and Pt-L$_3$ edges and confirm the predominant presence of alloy clusters that are highly dispersed and uniform in composition.

Catalytic Assessment of Reactivity and Encapsulation

Metal cluster confinement within zeolites precludes access by certain reactants or poisons to intracrystalline active clusters. Such restricted access also serves to retain large products until they convert to smaller species that can egress by diffusion, while the small intracrystalline voids can stabilize specific transition states. In all cases, these effects are dictated by the size of the voids and their connecting apertures in a given microporous framework. Here, such zeolite shape-selective properties are exploited by measuring oxidative dehydrogenation (ODH) turnover rates of a small molecule (ethanol, 0.40 nm kinetic diameter) on samples exposed to a large organosulfur molecule that poisons metal surfaces (dibenzothiophene, DBT; 0.9 nm kinetic diameter) to estimate the extent that bimetallic clusters reside within zeolite crystals. Organosulfur compounds such as DBT irreversibly adsorb onto Au, Pd, and Pt surfaces, forming unreactive species that block active sites. Consequently, ethanol ODH turnover rates on metal-$SiO_2$ samples and extracrystalline bimetallic clusters in metal-NaLTA samples would be suppressed by DBT, while clusters protected by NaLTA pore apertures (0.42 nm) would retain their ODH rates because they cannot be reached by DBT. The rate differences upon contact with DBT then provide a measure of the selectivity of metal encapsulation within intracrystalline domains.

Alkanol ODH reactions form alkanals as primary products. These alkanals can undergo subsequent reactions with alkanols to form hemiacetals or alkoxyalkanols and then dialkoxyalkanes and carboxylic acids through secondary dehydrogenation or condensations reactions. These secondary reactions do not affect measured turnover rates, because each product molecule formed involves a single ODH event, in which an alkanal forms via kinetically-relevant β-H abstraction from an adsorbed alkoxide by chemisorbed oxygen. The low conversions prevalent in this study (<5%) minimize secondary reactions and lead to high acetaldehyde selectivities (>95%, C-basis).

Ethanol oxidative dehydrogenation (ODH) turnover rates were measured on catalyst powders first diluted 10-fold by mass with fumed $SiO_2$ (CAB-O-SIL® HS-5, 310 m$^2$ g$^{-1}$) and then pressed into pellets and sieved to retain 180-250 μm aggregates. These diluted samples were then mixed in a 1:1 mass ratio with 180-250 μm acid-washed quartz granules to prevent any temperature gradients caused by exothermic ODH reactions. Catalysts were placed on a porous quartz frit within a quartz tube (10 mm O.D.). Samples were heated in 20% $O_2$/He (1.67 cm$^3$ g$^{-1}$ s$^{-1}$) from ambient temperature to 393 K (at 0.033 K s$^{-1}$) and held at that temperature for rate measurements. Liquid ethanol and deionized water were vaporized into flowing $O_2$/He streams at 393 K using liquid syringe pumps (Cole Parmer, 60061 Series). He and $O_2$ flow rates were adjusted with mass flow controllers (Porter Instrument) to achieve the desired pressures (4 kPa alkanol, 9 kPa $O_2$, 87.5 kPa He, and 0.5 kPa $H_2O$). Water forms as an ODH product and can have a co-catalytic effect. Thus, water was added to maintain a constant concentration of all species throughout the catalyst bed, thereby ensuring differential conditions. Alkanol conversions were kept below 5% and transfer lines were heated to 393 K to avoid condensation.

Turnover rates are defined as the molar ethanol conversion rates per surface metal atom estimated from the dispersion values defined in Equation 3. Product formation was not detectable on NaLTA, fumed silica, and empty reactors. Turnover rates were extrapolated to the start of each experiment. Effluent concentrations were measured by gas chromatography (Shimadzu GC-2014) using a methyl-silicone capillary column (HP-1; 50 m×0.32 mm, 1.05 μm film thickness) and a flame ionization detector.

Metal-NaLTA samples were exposed ex-situ to dibenzothiophene (DBT), an organosulfur poison that irreversibly titrates noble metal surfaces, before their use in ethanol ODH reactions. Ex-situ treatments exposed metal-NaLTA and metal-$SiO_2$ samples to DBT dissolved in liquid ethanol (300 cm$^3$ g$^{-1}$; DBT/metal molar ratio of 6) at ambient temperature for 4 h with magnetic agitation (6.7 Hz). The samples were then filtered and treated in ambient air at 343 K for 12 h, and used in ethanol ODH reactions at 393 K. Control samples were also prepared through an identical procedure without DBT and used for ethanol ODH.

Ethanol (0.40 nm kinetic diameter), but not DBT (0.9 nm), can diffuse through the apertures of NaLTA (0.42 nm). Thus, the extent of deactivation caused by exposure to DBT provides an assessment of the fraction of metal surfaces that are confined within zeolite crystals and protected from any large molecules present in the extracrystalline regions. A comparison of rates before and after exposure to DBT on metal-NaLTA and metal-$SiO_2$ samples then indicates the fraction of the active surfaces present at extracrystalline locations and thus the selectivity of the encapsulation.

Samples were exposed to DBT as described herein above before ODH rate measurements at 393 K. ODH rates were also measured on samples that were not contacted with DBT (denoted as "control samples"), but treated otherwise identically. ODH turnover rates measured on these controls ($r_{ODH}$) and on samples exposed to DBT (r ODH, DBT) are used to define a parameter $\Lambda_{DBT}$ according to Equation (4):

$$\Lambda_{DBT,i} = \frac{r_{ODH,DBT}}{r_{ODH}} \quad (4)$$

where i identifies the specific sample (e.g., $Au_{50}Pd_{50}$NaLTA, Pt/$SiO_2$). The value of $\Lambda_{DBT,i}$ reflects the fraction of the active surfaces that remain active for ODH after DBT exposure. A $\Lambda_{DBT,i}$ value of unity would reflect fully protected clusters, while a value of zero is expected if every active surface atom is accessible to and fully deactivated by DBT. Metal clusters that are encapsulated inside zeolites should be inaccessible to DBT and thus protected from deactivation, while metal clusters outside the zeolite crystals should be accessible to and deactivated by DBT. Exposure to DBT thus selectively suppresses the contribution to the ODH rate that originates from extrazeolite clusters. As a result, the value of $\Lambda_{DBT,i}$ is proportional to the fraction of encapsulated clusters in metal-zeolite samples. Values of $r_{ODH}$ and $\Lambda_{DBT,i}$ for Au, Pd, and Pt clusters supported on mesoporous $SiO_2$ and a representative group of bimetallic samples are shown in Table 3.

TABLE 3

| Sample | $r_{ODH}$ ($10^{-3}$ s$^{-1}$ mol$_{surf\text{-}metal}^{-1}$)[a] | $\Lambda_{DBT}$[b] |
| --- | --- | --- |
| $Au_{50}Pd_{50}$NaLTA | 110 | 0.97 |
| $Au_{50}Pt_{50}$NaLTA | 210 | 0.95 |
| $Pd_{65}Pt_{35}$NaLTA | 280 | 0.98 |
| Au/$SiO_2$ | 12 | 0.11 |
| Pd/$SiO_2$ | 320 | 0.03 |
| Pt/$SiO_2$ | 490 | 0.04 |

[a] Ethanol ODH turnover rates of samples agitated in EtOH (300 cm$^3$ g$^{-1}$) at ambient temperature for 4 h, treated in ambient air at 343 K for 12 h, then used in reaction (393 K under 9 kPa $O_2$, 4 kPa EtOH, and 0.5 kPa $H_2O$).
[b] $r_{ODH, DBT}/r_{ODH}$ (Equation 4), where $r_{ODH, DBT}$ is the ethanol ODH rate of analogously treated samples but with DBT dissolved in the EtOH at a 6:1 DBT:metal molar ratio. Reaction turnover rates are defined as the number of moles of reactant converted per time normalized by the number of exposed surface metal atoms estimated by TEM (Equation 3).

Ethanol ODH turnover rates were much more weakly suppressed by contact with DBT on metal-NaLTA ($\Lambda_{DBT,i}$=0.95-0.98) than on metal-SiO$_2$ ($\Lambda_{DBT,i}$=0.03-0.11) samples (Table 3), indicating that (a) DBT effectively titrates unprotected noble metal surfaces; and (b) most of the metal clusters reside within LTA crystals in metal-NaLTA samples. The small residual ODH activity on SiO$_2$-supported samples, even after contact with excess DBT (6:1 DBT:metal molar ratio), may reflect steric effects that hinder access to remaining open sites as DBT-derived species reach near-saturation coverages. The remarkable resistance to DBT poisoning in metal-NaLTA samples, evident in their $\Lambda_{DBT,i}$ values near unity (0.95-0.98) (Table 3), provides compelling evidence for the near complete encapsulation of these bimetallic clusters, as also found for monometallic clusters encapsulated within LTA and other zeolites using similar hydrothermal synthesis protocols.

It is concluded that the hydrothermal encapsulation method described herein can be more generally applied to prepare bimetallic clusters which are small and uniform in size, highly stable against thermal sintering, homogeneously distributed in composition, and selectively encapsulated within zeolite crystals.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All ranges disclosed herein are inclusive of the endpoints and are independently combinable. Whenever a numerical range with a lower limit and an upper limit are disclosed, any number falling within the range is also specifically disclosed.

All documents cited in this application are herein incorporated by reference in their entirety to the extent such disclosure is not inconsistent with this text.

What is claimed is:

1. An aluminosilicate zeolite having an alloyed bimetallic cluster encapsulated in the pores of the aluminosilicate zeolite, with the zeolite being a small pore zeolite or a medium pore zeolite.

2. The aluminosilicate zeolite of claim 1, wherein the aluminosilicate zeolite is a small pore zeolite having a CHA, ERI, GIS, KFI, LEV, LTA, RTH, or SOD framework type.

3. The aluminosilicate zeolite of claim 2, wherein the small pore zeolite has the framework type LTA.

4. The aluminosilicate zeolite of claim 1, wherein the aluminosilicate zeolite is a medium pore zeolite having an EUO, FER, HEU, MEL, MFI, MFS, MTT, MTW, or TON framework type.

5. The aluminosilicate zeolite of claim 1, wherein the alloyed bimetallic cluster has a dispersity index of 1 to 1.5.

6. The aluminosilicate zeolite of claim 1, wherein metals in the alloyed bimetallic cluster are selected from Groups 8 to 12 of the Periodic Table.

7. The aluminosilicate zeolite of claim 6, wherein a collective amount of metals of Groups 8 to 12 is from 0.1 to 5.0 wt. % of the total weight of composite.

8. The composition of claim 1, wherein the alloyed bimetallic cluster comprises gold and palladium, gold and platinum, or palladium and platinum.

9. A method of synthesizing the aluminosilicate zeolite of claim 1, the method comprising the steps of:
   (a) preparing a reaction mixture capable of forming the zeolite, the reaction mixture comprising: a source of silicon oxide; a source of aluminum oxide; a source of a Group 1 or 2 metal (X); hydroxide ions; sources of a first metal precursor ($M_1$) and a second metal precursor ($M_2$) of Groups 8 to 12 of the Periodic Table of the Elements; a ligating agent (L) having a thiol group and an alkoxysilyl group; and water;
   (b) heating the reaction mixture under crystallization conditions including a temperature of 85° C. to 180° C. and a time from 5 to 250 hours until crystals of the aluminosilicate zeolite are formed;
   (c) recovering the aluminosilicate zeolite from step (b):
   (d) contacting the aluminosilicate zeolite of step (c) with oxygen under oxidative conditions including a temperature of 250° C. to 500° C. and a time of 0.5 to 5 h; and
   (e) contacting the oxidized aluminosilicate zeolite of step (d) with hydrogen under reductive conditions including a temperature of 250° C. to 500° C. and a time of 0.5 to 5 h.

10. The method of claim 9, wherein the aluminosilicate zeolite is zeolite is prepared from a reaction comprising, in terms of mole ratios, the following:

| | |
|---|---|
| SiO$_2$/Al$_2$O$_3$ | ≥1 |
| X/SiO$_2$ | 0.25 to 1.00 |
| OH/SiO$_2$ | 0.25 to 1.00 |
| (M$_1$ + M$_2$)/SiO$_2$ | 0.005 to 0.025 |
| L/SiO$_2$ | 0.02 to 0.25 |
| H$_2$O/SiO$_2$ | ≥50. |

11. The method of 9, wherein the reaction mixture is substantially free of organotemplate materials.

12. The method of claim 9, wherein the ligating agent is selected from the group consisting of 3-mercaptopropyltrimethoxysilane, 3-mercaptopropyltriethoxysilane, 3-mercaptopropylmethyldimethoxysilane, (mercaptomethyl)dimethylethoxysilane, mercaptomethyltrimethoxysilane, and combinations thereof.

13. A process for converting a feedstock comprising an organic compound to a conversion product which comprises the step of contacting the feedstock with a catalyst, at organic compound conversion conditions, the catalyst comprising the aluminosilicate zeolite of claim 1.

14. A process for selectively reducing nitrogen oxides (NO$_x$), the method comprising contacting a gaseous stream containing NO$_x$ with a catalyst comprising the aluminosilicate zeolite of claim 1.

* * * * *

UNITED STATES PATENT AND TRADEMARK OFFICE
CERTIFICATE OF CORRECTION

| | | |
|---|---|---|
| PATENT NO. | : 10,512,904 B2 | Page 1 of 1 |
| APPLICATION NO. | : 15/602797 | |
| DATED | : December 24, 2019 | |
| INVENTOR(S) | : Trenton Otto, Enrique Iglesia and Stacey Ian Zones | |

It is certified that error appears in the above-identified patent and that said Letters Patent is hereby corrected as shown below:

In the Claims

Claim 10, Column 24, Line 31, delete the second occurrence of "zeolite is"

Signed and Sealed this
Fourth Day of August, 2020

Andrei Iancu
*Director of the United States Patent and Trademark Office*